United States Patent
Bagga et al.

(10) Patent No.: US 10,478,528 B2
(45) Date of Patent: *Nov. 19, 2019

(54) BONE GRAFT IMPLANTS CONTAINING ALLOGRAFT

(71) Applicant: PROSIDYAN, INC., Warren, NJ (US)

(72) Inventors: Charanpreet S. Bagga, Basking Ridge, NJ (US); Steven B. Jung, Rolla, MO (US); Hyun W. Bae, Los Angeles, CA (US)

(73) Assignee: PROSIDYAN, INC., Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/200,801

(22) Filed: Jul. 1, 2016

(65) Prior Publication Data

US 2016/0310638 A1 Oct. 27, 2016

Related U.S. Application Data

(63) Continuation of application No. 13/830,851, filed on Mar. 14, 2013, now Pat. No. 9,381,274.

(51) Int. Cl.
| | |
|---|---|
| *A61L 27/54* | (2006.01) |
| *A61L 27/42* | (2006.01) |
| *A61L 27/56* | (2006.01) |
| *A61L 27/36* | (2006.01) |
| *A61L 27/46* | (2006.01) |
| *A61L 27/12* | (2006.01) |
| *A61L 27/24* | (2006.01) |
| *A61L 27/32* | (2006.01) |
| *A61L 27/34* | (2006.01) |
| *A61L 27/58* | (2006.01) |

(52) U.S. Cl.
CPC ............ *A61L 27/54* (2013.01); *A61L 27/12* (2013.01); *A61L 27/24* (2013.01); *A61L 27/32* (2013.01); *A61L 27/34* (2013.01); *A61L 27/365* (2013.01); *A61L 27/3608* (2013.01); *A61L 27/425* (2013.01); *A61L 27/427* (2013.01); *A61L 27/46* (2013.01); *A61L 27/56* (2013.01); *A61L 27/58* (2013.01); *A61L 2300/104* (2013.01); *A61L 2300/112* (2013.01); *A61L 2300/404* (2013.01); *A61L 2300/414* (2013.01); *A61L 2300/64* (2013.01); *A61L 2430/02* (2013.01)

(58) Field of Classification Search
None
See application file for complete search history.

(56) References Cited

U.S. PATENT DOCUMENTS

| | | |
|---|---|---|
| 4,693,721 A | 9/1987 | Ducheyne |
| 4,861,733 A | 8/1989 | White |
| 5,030,233 A | 7/1991 | Ducheyne |
| 5,429,996 A | 7/1995 | Kaneko |
| 5,626,861 A | 5/1997 | Laurencin et al. |
| 5,776,193 A | 7/1998 | Kwan et al. |
| 6,051,247 A | 4/2000 | Hench et al. |
| 6,054,400 A | 4/2000 | Brink et al. |
| 6,139,585 A | 10/2000 | Li |
| 6,398,814 B1 | 6/2002 | Paasimaa |
| 6,482,444 B1 | 11/2002 | Bellantone et al. |
| 6,783,712 B2 | 8/2004 | Slivka et al. |
| 6,808,585 B2 | 10/2004 | Boyce et al. |
| 6,902,584 B2 | 6/2005 | Kwan et al. |
| 6,955,716 B2 | 10/2005 | Xu |
| 7,018,460 B2 | 3/2006 | Xu |
| 7,241,486 B2 | 7/2007 | Pirhonen |
| 7,621,963 B2 | 11/2009 | Simon et al. |
| 7,767,221 B2 | 8/2010 | Lu et al. |
| 7,964,206 B2 | 6/2011 | Suokas et al. |
| 8,093,166 B2 | 1/2012 | Moimas et al. |
| 8,153,148 B2 | 4/2012 | Maspero et al. |
| 8,163,030 B2 | 4/2012 | Maspero et al. |
| 8,303,967 B2 | 11/2012 | Clineff et al. |
| 8,449,904 B1 | 5/2013 | Jung |
| 8,506,981 B1 | 8/2013 | Borden |
| 9,045,362 B2 * | 6/2015 | Jung ............... C03C 4/0007 |
| 2001/0014830 A1 | 8/2001 | Kwan et al. |
| 2002/0076429 A1 | 6/2002 | Wironen et al. |
| 2002/0160175 A1 | 10/2002 | Pirhonen |
| 2003/0075822 A1 | 4/2003 | Slivka et al. |
| 2003/0120348 A1 | 6/2003 | Brosnahan et al. |
| 2003/0198660 A1 | 10/2003 | Janas et al. |
| 2004/0009598 A1 | 1/2004 | Hench et al. |
| 2005/0090905 A1 | 4/2005 | Hawkins et al. |

(Continued)

FOREIGN PATENT DOCUMENTS

| | | |
|---|---|---|
| EP | 1660146 A1 | 5/2006 |
| EP | 1729675 A2 | 12/2006 |

(Continued)

OTHER PUBLICATIONS

Pirhonen, E., et al., Key Engineering Materials 240-242: 237-240 (2003).*

Author Unknown, International Search Report dated Oct. 10, 2014, International Application No. PCT/US2014/026965, pp. 1-14.

Griffon, D.J. et al., "Early dissolution of a morsellised impacted silicate-free bioactive glass in metaphyseal defects", J. Biomed. Matter Res., 2001: 58(5), pp. 638-644.

(Continued)

*Primary Examiner* — David J Blanchard
*Assistant Examiner* — Daniel F. Coughlin
(74) *Attorney, Agent, or Firm* — Farber LLC

(57) ABSTRACT

Synthetic, bioactive ultra-porous bone graft materials having an engineered porosity, and implants formed from such materials are provided. In particular, these implants comprise bioactive glass and incorporate allograft material for osteoinduction. The implants are suitable for bone tissue regeneration and/or repair.

9 Claims, 11 Drawing Sheets

(56) References Cited

U.S. PATENT DOCUMENTS

| | | |
|---|---|---|
| 2005/0118236 A1 | 6/2005 | Qiu et al. |
| 2005/0249773 A1 | 11/2005 | Maspero et al. |
| 2006/0067969 A1 | 3/2006 | Lu |
| 2006/0093645 A1 | 5/2006 | Janas et al. |
| 2006/0121609 A1 | 6/2006 | Yannas et al. |
| 2006/0280775 A1 | 6/2006 | Ashammakhi |
| 2007/0141110 A1 | 2/2007 | Stone |
| 2007/0141111 A1 | 6/2007 | Suokas |
| 2007/0142916 A1 | 6/2007 | Olson et al. |
| 2007/0240601 A1 | 10/2007 | Chou et al. |
| 2008/0038534 A1 | 2/2008 | Zenati et al. |
| 2008/0086199 A1* | 4/2008 | Dave .............. A61L 27/18 623/1.42 |
| 2008/0187571 A1 | 8/2008 | Clineff |
| 2009/0208428 A1 | 8/2009 | Hill et al. |
| 2010/0010513 A1 | 1/2010 | Yun et al. |
| 2010/0136086 A1 | 6/2010 | Day et al. |
| 2010/0179662 A1 | 7/2010 | Verne et al. |
| 2010/0179667 A1* | 7/2010 | Day .............. A61L 27/10 623/23.72 |
| 2010/0278902 A1 | 11/2010 | Jallot et al. |
| 2011/0066242 A1 | 3/2011 | Lu et al. |
| 2011/0081693 A1 | 4/2011 | Denry |
| 2011/0082564 A1 | 4/2011 | Liu et al. |
| 2011/0106255 A1 | 5/2011 | Liu et al. |
| 2011/0106272 A1 | 5/2011 | Liu |
| 2011/0140316 A1 | 6/2011 | Bagga et al. |
| 2011/0144763 A1 | 6/2011 | Bagga et al. |
| 2011/0144764 A1 | 6/2011 | Bagga et al. |
| 2011/0204537 A1 | 8/2011 | Liu et al. |
| 2011/0206828 A1 | 8/2011 | Liu et al. |
| 2011/0217388 A1 | 9/2011 | Greenspan et al. |
| 2011/0256203 A1 | 10/2011 | Kim et al. |
| 2012/0164187 A1 | 6/2012 | Ollila et al. |
| 2012/0203355 A1 | 8/2012 | Liu |
| 2012/0219635 A1 | 8/2012 | Liu |
| 2012/0265167 A1 | 10/2012 | Simonson et al. |
| 2012/0276164 A1 | 11/2012 | Tuomimen et al. |
| 2012/0288699 A1 | 11/2012 | Ahlberg et al. |

FOREIGN PATENT DOCUMENTS

| | | |
|---|---|---|
| EP | 1733746 A2 | 12/2006 |
| EP | 2040765 A2 | 4/2009 |
| WO | 2005/018698 A1 | 3/2005 |
| WO | 2005/086706 A2 | 9/2005 |
| WO | 2006/118554 A1 | 11/2006 |
| WO | 2008/002682 A2 | 1/2008 |
| WO | 2011/053725 A1 | 5/2011 |

OTHER PUBLICATIONS

Kyung Mi Woo et al., "Comparative Evaluation of Nanofibrous Scaffolding for Bone Regeneration in Critical-Size Calvarial Defects", Tissue Engineering: Part A, vol. 15, No. 8, 2009, pp. 2155-2162.

Woodruff et al., "Bone tissue engineering: from bench to bedside", Materials Today, vol. 15, No. 10, Oct. 2012, pp. 430-435.

Antoine Laurent, Extended European Search Report, European Application No. 14767434.5, filed Mar. 14, 2014, pp. 1-8.

* cited by examiner

BONE GRAFT IMPLANTS CONTAINING ALLOGRAFT

CROSS-REFERENCE TO RELATED APPLICATIONS

This application is a continuation of U.S. patent application Ser. No. 13/830,851, filed Mar. 14, 2013 and entitled "BONE GRAFT IMPLANTS CONTAINING ALLOGRAFT", now U.S. Pat. No. 9,381,274, the contents of which are herein incorporated in their entirety by reference.

FIELD

The present disclosure relates generally to bone graft materials and methods of using such materials as implants for bone tissue regrowth. More particularly, the present disclosure relates to bioactive porous bone graft implants that incorporate allograft materials for osteoinduction suitable for bone tissue regeneration and/or repair, as well as methods of use.

BACKGROUND

The role of bone graft materials in clinical applications to aid the healing of bone has been well documented over the years. Most bone graft materials that are currently available, however, have failed to deliver the anticipated results necessary to make these materials a routine therapeutic application in reconstructive surgery. Improved bone graft materials for forming bone tissue implants that can produce reliable and consistent results are therefore still needed and desired.

In recent years intensive studies have been made on bone graft materials in the hopes of identifying the key features necessary to produce an ideal bone graft implant, as well as to proffer a theory of the mechanism of action that results in successful bone tissue growth. At least one recent study has suggested that a successful bone tissue scaffold should consider the physicochemical properties, morphology and degradation kinetics of the bone being treated. ("Bone tissue engineering: from bench to bedside", Woodruff et al., Materials Today, 15(10): 430-435 (2012)). According to the study, porosity is necessary to allow vascularization, and the desired scaffold should have a porous interconnected pore network with surface properties that are optimized for cell attachment, migration, proliferation and differentiation. At the same time, the scaffold should be biocompatible and allow flow transport of nutrients and metabolic waste. Just as important is the scaffold's ability to provide a controllable rate of biodegradation to compliment cell and/or tissue growth and maturation. Finally, the ability to model and/or customize the external size and shape of the scaffold is to allow a customized fit for the individual patient is of equal importance.

Woodruff, et. al. also suggested that the rate of degradation of the scaffold must be compatible with the rate of bone tissue formation, remodeling and maturation. Recent studies have demonstrated that initial bone tissue ingrowth does not equate to tissue maturation and remodeling. According to the study, most of the currently available bone graft implants are formulated to degrade as soon as new tissue emerges, and at a faster rate than the new bone tissue is able to mature, resulting in less than desirable clinical outcomes.

Other researchers have emphasized different aspects as the core features of an ideal bone graft implant. For example, many believe that the implant's ability to provide adequate structural support or mechanical integrity for new cellular activity is the main factor to achieving clinical success, while others emphasize the role of porosity as the key feature. The roles of porosity, pore size and pore size distribution in promoting revascularization, healing, and remodeling of bone have long been recognized as important contributing factors for successful bone grafting implants. Many studies have suggested an ideal range of porosities and pore size distributions for achieving bone graft success. However, as clinical results have shown, a biocompatible bone graft having the correct structure and mechanical integrity for new bone growth or having the requisite porosities and pore distributions alone does not guarantee a good clinical outcome. What is clear from this collective body of research is that the ideal bone graft implant should possess a combination of structural and functional features that act in synergy to allow the bone graft implant to support the biological activity and an effective mechanism of action as time progresses.

Currently available bone graft implants fall short of meeting these requirements. That is, many bone graft implants tend to suffer from one or more of the problems previously mentioned, while others may have different, negatively associated complications or shortcomings. One example of such a graft implant is autograft implants. Autograft implants have acceptable physical and biological properties and exhibit the appropriate mechanical structure and integrity for bone growth. However, the use of autogenous bone requires the patient to undergo multiple or extended surgeries, consequently increasing the time the patient is under anesthesia, and leading to considerable pain, increased risk of infection and other complications, and morbidity at the donor site.

When it comes to synthetic bone graft substitutes, the most rapidly expanding category consists of products based on calcium sulfate, hydroxyapatite and tricalcium phosphate. Whether in the form of injectable cements, blocks or morsels, these materials have a proven track record of being effective, safe bone graft substitutes for selected clinical applications. Recently, new materials such as bioactive glass ("BAG") have become an increasingly viable alternative or supplement to natural bone-derived graft materials. In comparison to autograft implants, these new synthetic implants have the advantage of avoiding painful and inherently risky harvesting procedures on patients. Also, the use of these synthetic, non-bone derived materials can reduce the risk of disease transmission. Like autograft and allograft implants, these new artificial implants can serve as osteoconductive scaffolds that promote bone regrowth. Preferably, the graft implant is resorbable and is eventually replaced with new bone tissue.

Many artificial bone grafts available today comprise materials that have properties similar to natural bone, such as implants containing calcium phosphates. Exemplary calcium phosphate implants contain type-B carbonated hydroxyapatite whose composition in general may be described as $(Ca_5(PO_4)_{3x}(CO_3)_x(OH))$. Calcium phosphate ceramics have been fabricated and implanted in mammals in various forms including, but not limited to, shaped bodies and cements. Different stoichiometric implants, such as hydroxyapatite (HA), tricalcium phosphate (TCP), tetracalcium phosphate (TTCP), and other calcium phosphate (CaP) salts and minerals have all been employed in attempts to match the adaptability, biocompatibility, structure, and strength of natural bone. Although calcium phosphate based materials are widely accepted, they lack the ease of handling, flexibility and capacity to serve as a liquid carrier/storage media necessary to be used in a wide array of clinical applications. Calcium phosphate materials are inherently rigid, and to facilitate handling are generally provided as part of an admixture with a carrier material; such admixtures typically have an active calcium phosphate ingredient to carrier volume ratio of about 50:50, and may have a ratio as low as 10:90.

As previously mentioned, the roles of porosity, pore size and pore size distribution in promoting revascularization, healing, and remodeling of bone have been recognized as important contributing factors for successful bone grafting. Yet currently available bone graft implants still lack the requisite chemical and physical properties necessary for an ideal graft implant. For instance, currently available graft implants tend to resorb too quickly (e.g., within a few weeks), while some take too long (e.g., over years) to resorb due to the implant's chemical composition and structure. For example, certain implants made from hydroxyapatite tend to take too long to resorb, while implants made from calcium sulfate or β-TCP tend to resorb too quickly. Further, if the porosity of the implant is too high (e.g., around 90%), there may not be enough base material left after resorption has taken place to support osteoconduction. Conversely, if the porosity of the implant is too low (e.g., 10%,) then too much material must be resorbed, leading to longer resorption rates. In addition, the excess material means there may not be enough room left in the residual graft implant for cell infiltration. Other times, the graft implants may be too soft, such that any kind of physical pressure exerted on them during clinical usage causes them to lose the fluids retained by them.

Accordingly, there continues to be a need for better bone graft implants. For instance, it would be desirable to provide improved bone graft implants offering the benefits just described, and in a form that is even easier to handle and allows even better clinical results. Embodiments of the present disclosure address these and other needs.

SUMMARY

The present disclosure provides bone graft materials and implants formed from these materials that are engineered with a combination of structural and functional features that act in synergy to allow the bone graft implant to support cell proliferation and new tissue growth over time. The implants serve as cellular scaffolds to provide the necessary porosity and pore size distribution to allow proper vascularization, optimized cell attachment, migration, proliferation, and differentiation. The implants are formed of synthetic materials that are biocompatible and offer the requisite mechanical integrity to support continued cell proliferation throughout the healing process. In addition, the materials are formulated for improved clinical handling and allow easy modeling and/or customization of the external size and shape to produce a customized implant for the anatomic site.

In one embodiment, a porous, composite bone graft implant is provided. The implant may comprise a first component comprising a bioactive glass and a second component comprising allograft material. Each of the components may have a different resorption capacity than the other component. The implant may further comprise a pore size distribution including pores characterized by pore diameters ranging from about 100 nanometers to about 1 millimeter. The bioactive glass may comprise bioactive glass fibers, bioactive glass granules, or combinations thereof. The allograft material may be provided as demineralized bone matrix, bone chips, stem-cell preserved bone chips, or human-derived collagen.

In another embodiment, a porous, composite bone graft implant is provided. The implant may comprise a first component comprising bioactive glass fibers and a second component comprising allograft material. Each of the components may have a different resorption capacity than the other component. The implant may further comprise a pore size distribution including pores characterized by pore diameters ranging from about 100 nanometers to about 1 millimeter. The allograft material may be provided as demineralized bone matrix, bone chips, stem-cell preserved bone chips, or human-derived collagen. The implant may further include bioactive glass granules. Furthermore, the implant may be encased in bioactive glass, glass-ceramic, ceramic, or polymer.

In still another embodiment, a porous, composite bone graft implant is provided. The implant may comprise a first component comprising bioactive glass granules and a second component comprising allograft material. Each of the components may have a different resorption capacity than the other component. The implant may further comprise a pore size distribution including pores characterized by pore diameters ranging from about 100 nanometers to about 1 millimeter. The allograft material may be provided as demineralized bone matrix, bone chips, stem-cell preserved bone chips, or human-derived collagen. The implant may further comprise bioactive glass fibers. Furthermore, the implant may be encased in bioactive glass, glass-ceramic, ceramic, or polymer.

In even still another embodiment, a composite bone graft implant is provided. The implant may comprise a bioactive glass material, allograft material, and a carrier material. The implant may comprise a pore size distribution including pores characterized by pore diameters ranging from about 100 nanometers to about 1 millimeter. The bioactive glass may comprise bioactive glass fibers, bioactive glass granules, or combinations thereof. The allograft material may be provided as demineralized bone matrix, bone chips, stem-cell preserved bone chips, or human-derived collagen. The implant may be provided as a putty or a foam.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

Figure 1A:
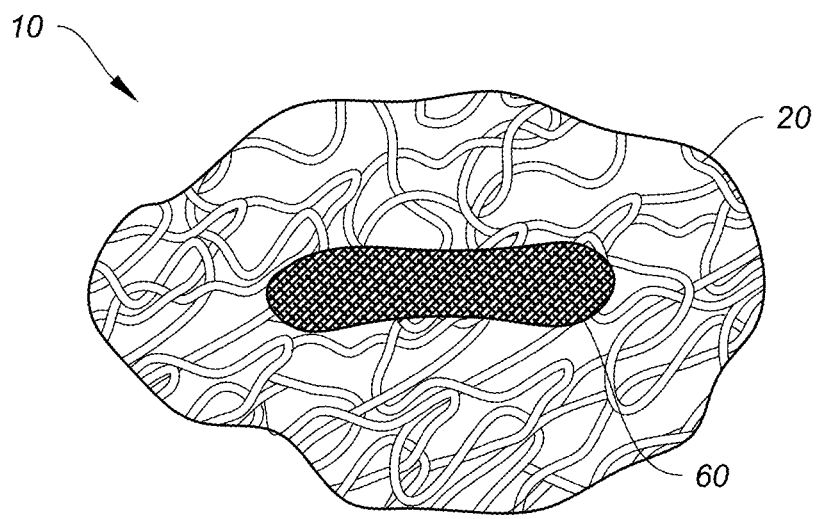
FIG. 1A illustrates a partial cutaway view of an exemplary embodiment of a bone graft implant of the present disclosure in which the implant comprises a fibrous matrix containing allograft.

The foregoing and other features of the present disclosure will become apparent to one skilled in the art to which the present disclosure relates upon consideration of the following description of exemplary embodiments with reference to the accompanying drawings.

DETAILED DESCRIPTION OF THE EMBODIMENTS

The present disclosure provides bone graft materials and implants formed from these materials that are engineered with a combination of structural and functional features that act in synergy to allow the bone graft implant to support cell proliferation and new tissue growth over time. The implants provide the necessary porosity and pore size distribution to allow proper vascularization, optimized cell attachment, migration, proliferation, and differentiation. The implants are formed of synthetic materials that are biocompatible and offer the requisite mechanical integrity to support continued cell proliferation throughout the healing process. In addition, the materials are formulated for improved handling and allow easy modeling and/or customization of the external size and shape of the implants to produce a customized implant for the anatomic site.

The bone graft implants may be formed of a synthetic material that is both biocompatible and bioabsorbable or bioresorbable. In addition, the synthetic material may be bioactive. In one embodiment, the material may be a material that is bioactive and forms a calcium phosphate layer on its surface upon implantation. In another embodiment, the material may comprise a bioactive glass ("BAG"). Suitable bioactive glasses include sol gel derived bioactive glass, melt derived bioactive glass, silica based bioactive glass, silica free bioactive glass such as borate based bioactive glass and phosphate based bioactive glass, crystallized bioactive glass (either partially or wholly), and bioactive glass containing trace elements or metals such as copper, zinc, strontium, magnesium, zinc, fluoride, mineralogical calcium sources, and the like. Examples of sol gel derived bioactive glass include S70C30 characterized by the general implant of 70 mol % $SiO_2$, 30 mol % CaO. Examples of melt derived bioactive glass include 45S5 characterized by the general implant of 46.1 mol % $SiO_2$, 26.9 mol % CaO, 24.4 mol % $Na_2O$ and 2.5 mol % $P_2O_5$, S53P4, and 58S characterized by the general implant of 60 mol % $SiO_2$, 36 mol % CaO and 4 mol % $P_2O_5$. Another suitable bioactive glass may also be 13-93 bioactive glass.

The bioactive glass forms the base material from which the engineered bone graft implants of the present disclosure are composed. The bioactive glass may take the form of fibers, granules, or a combination of both. By the term granules, what is meant is at least one fragment or more of material having a non-rod shaped form, such as a rounded, spherical, globular, or irregular body.

The bioactive glass may be provided in a materially pure form. Additionally, the bioactive glass may be mixed with a carrier for better clinical handling, such as to make a putty or foam implant. A pliable implant in the form of a putty may be provided by mixing the bioactive glass with a flowable or viscous carrier. A foam implant may be provided by embedding the bioactive glass in a porous matrix such as collagen (either human or animal derived) or porous polymer matrix. One of the advantages of a foam implant is that the porous carrier can also act as a site for attaching cells and growth factors, and may lead to a better managed healing.

The carrier material may be porous and may help contribute to healing. For example, the carrier material may have the appropriate porosity to create a capillary effect to bring in cells and/or nutrients to the implantation site. The carrier material may also possess the chemistry to create osmotic or swelling pressure to bring in nutrients to the site and resorb quickly in the process. For instance, the carrier material may be a polyethylene glycol (PEG) which has a high affinity to water.

The bioactive glass may be manufactured by electrospinning, or by laser spinning for uniformity. For example, where the material is desired in a fibrous form, laser spinning would produce fibers of uniform diameters. Further, the bioactive glass fibers may be formed having varying diameters and/or cross-sectional shapes, and may even be drawn as hollow tubes. Additionally, the fibers may be meshed, woven, intertangled and the like for provision into a wide variety of shapes.

The bone graft material may be engineered with fibers having varying resorption rates. The resorption rate of a fiber is determined or controlled by its material composition and by its diameter. The material composition may result in a slow reacting vs. faster reacting product. Similarly, smaller diameter fibers can resorb faster than larger diameter fibers of the same implant. Also, the overall porosity of the material can affect resorption rate. Materials possessing a higher porosity mean there is less material for cells to remove. Conversely, materials possessing a lower porosity mean cells have to do more work, and resorption is slower. Accordingly, the bone graft implants may contain fibers that have the appropriate material composition as well as diameter for optimal performance. A combination of different fibers may be included in the implant in order to achieve the desired result.

Equally as important as the material composition and diameter is the pore size distribution of the open porosity and in particular the surface area of the open porosity. The present bone graft implants provide not only an improved pore size distribution over other bone graft implants, but a higher surface area for the open pores. The larger surface area of the open porosity of the present implants drives faster resorption by body fluids, allowing the fluid better access to the pores.

Similar to the bioactive glass fibers, the inclusion of bioactive glass granules can be accomplished using particulates having a wide range of sizes or configurations to include roughened surfaces, very large surface areas, and the like. For example, granules may be tailored to include interior lumens with perforations to permit exposure of the surface of the granule's interior. Such granules would be more quickly absorbed, allowing a tailored implant characterized by differential resorbability. The perforated or porous granules could be characterized by uniform diameters or uniform perforation sizes, for example. The porosity provided by the granules may be viewed as a secondary range of porosity accorded the bone graft material or the implant formed from the bone graft material. By varying the size, transverse diameter, surface texture, and configurations of the bioactive glass fibers and granules, if included, the manufacturer has the ability to provide a bioactive glass bone graft implant with selectively variable characteristics that can greatly affect the function of the implant before and after it is implanted in a patient. The nano and micro sized pores provide superb fluid soak and hold capacity, which enhances the bioactivity and accordingly the repair process.

Due to the pliability of this fibrous graft material, these same bioactive glass fibers may be formed or shaped into fibrous clusters with relative ease. These clusters can be achieved with a little mechanical agitation of the bioactive glass fibrous material. The resultant fibrous clusters are extremely porous and can easily wick up fluids or other nutrients. Hence, by providing the bioactive glass material in the form of a porous, fibrous cluster, even greater clinical results and better handling can be achieved.

The formed and shaped bioactive glass materials of the present disclosure, either with or without sintering, share similar attributes with a finite density material that has been dictated by its processing and the fiber dimensions of the base material (e.g., diameter and length of the fibers) that resulted in the cluster formation. The ultra-porous clusters can possess nano, micro, meso, and macro porosity in a gradient throughout the cluster. Without limitation, a nanopore is intended to represent a pore having a diameter below about 1 micron and as small as 100 nanometers or smaller, a micropore is intended to represent a pore having a diameter between about 1 to 10 microns, a mesopore is intended to represent a pore having a diameter between about 10 to 100 microns, and a macropore is intended to represent a pore having a diameter greater than about 100 microns and as large as 1 mm or even larger. Under a consistent manufacturing process, the formed clusters of bioactive glass can be used with volumetric dosage to fill a bone defect. Any number of differently sized clusters can be provided for various clinical applications.

One of the benefits of providing an ultra-porous bioactive glass material in cluster form is that handling of the material can be improved. In one manner of handling the cluster of materials, the clusters may be packaged in a syringe with a carrier, and injected into the bone defect with ease. Another benefit is the additional structural effect of having a plurality clusters of fibers closely packed together, forming additional macrostructures to the overall scaffold of material. Like a sieve, the openings between individual clusters can be beneficial such as when a filter is desired for various nutrients in blood or bone marrow to concentrate certain desired nutrients at the implant location.

Of course, it is understood that, while the term cluster is used to describe the shape of the materials, such term is not intended to limit the invention to spherical shapes. In fact, the formed cluster shape may comprise any rounded or irregular shape, so long as it is not a rod shape. In the present disclosure, the term fibrous cluster represents a matrix of randomly oriented fibers of a range of sizes and length. Additional granules or particulates of material may be placed randomly inside this matrix to provide additional advantages. A variety of materials and structure can optionally be employed to control the rate of resoprtion, osteostimulation, osteogenesis, compression resistance, radiopacity, antimicrobial activity, rate of drug elution, and provide optimal clinical handling for a particular application.

The use of fused or hardened fiber clusters may be advantageous in some instances, because the fusing provides relative hardness to the clusters, thereby rendering the hardened clusters mechanically stronger. Their combination with the glass granules further enhances the structural integrity, mechanical strength, and durability of the implant. Because larger sized granules or clusters will tend to have longer resorption time, in previous cases the user had to sacrifice strength for speed. However, it is possible to provide larger sized granules or clusters to achieve mechanical strength, without significantly sacrificing the speed of resorption. To this end, ultra-porous clusters can be utilized as just described for fiber-based and glass-based clusters. Rather than using solid spheres or clusters, the present disclosure provides ultra-porous clusters that have the integrity that overall larger sized clusters provide, along with the porosity that allows for speed in resorption. These ultra-porous clusters will tend to absorb more nutrients, resorb quicker, and lead to much faster healing and remodeling of the defect.

In some embodiments, the fiber clusters may be partially or fully fused or hardened to provide hard clusters. Of course, it is contemplated that a combination of both fused fiber clusters (hard clusters) and unfused or loose fiber clusters (soft clusters) may be used in one application simultaneously. Likewise, combinations of putty, foam, clusters and other formulations of the fibrous graft material may be used in a single application to create an even more sophisticated porosity gradient and ultimately offer a better healing response. In some cases, solid porous granules of the bioactive glass material may also be incorporated into the implant.

As previously discussed, the ideal bone graft implant must possess a combination of features that act in synergy to allow the bone graft material to support the biological activity of tissue growth and mechanism of action as time progresses. It is known that porosities and pore size distribution play a critical role in the clinical success of bone graft materials. More specifically, the bone graft implant needs to include an appropriate pore size distribution to provide optimized cell attachment, migration, proliferation and differentiation, and to allow flow transport of nutrients and metabolic waste. In addition, in a porous structure the amount and size of the pores, which collectively form the pore size gradient, will be directly related to the mechanical integrity of the material as well as affect its resorption rate. Having a stratified porosity gradient will provide a more complex resorption profile for the bone graft material, and engineering the material with a suitable pore size gradient will avoid a resorption rate that is too fast or too slow.

As applicants have discovered, this desired pore size distribution includes a range of porosities that includes macro, meso, micro and nano pores. As previously mentioned, without limitation, a nanopore is intended to represent a pore having a diameter below about 1 micron and as small as 100 nanometers or smaller, a micropore is intended to represent a pore having a diameter between about 1 to 10 microns, a mesopore is intended to represent a pore having a diameter between about 10 to 100 microns, and a macropore is intended to represent a pore having a diameter greater than about 100 microns and as large as 1 mm or even larger. Accordingly, the bioactive glass material may be provided with variable degrees of porosity, and is preferably ultraporous. In one embodiment, the material may have a range of porosities including macro, meso, micro and nano pores. The resultant engineered implant may also include the same range of porosities, which could be provided as a porous network of matrices within the fibrous scaffold and around the material. Accordingly, porosity may be provided inherently by the actual bioactive glass material itself, as well as the matrices separating the material within the overall implant.

Another feature of the engineered bone graft implants of the present disclosure is their ability to provide mechanical integrity to support new tissue growth. Not only should the implant provide the appropriate biocompatibility and resorption rate, but the surface area should be maximized to fully support cell proliferation. The engineered implant can be selectively composed and structured to have differential or staged resorption capacity, while still being easily molded or shaped into clinically relevant shapes as needed for different surgical and anatomical applications. Additionally, these engineered implants may have differential bioresorbability, compression resistance and radiopacity, and can also maximize the content of active ingredient relative to carrier materials such as for example collagen.

The present disclosure provides improved bone graft materials and bone graft implants formed from these materials that are able to sustain tissue growth throughout the healing process. One of the deficiencies of currently available bone graft implants is their lack of ability to provide proper mechanical scaffolding while supporting cell proliferation over time. The engineered materials and implants of the present disclosure overcome this problem by providing, among other things, an appropriate combination of porosities (i.e., pore size distribution) and high surface area within a porous bioactive glass infrastructure that serves as an ideal scaffold for tissue growth. More importantly, the range of porosities is distributed throughout the porous bioactive glass infrastructure, which is able to support continued cell proliferation throughout the healing process.

Initially upon implantation, the engineered implants provide a network of macro, meso, micro and nano pores distributed within a fibrous bioactive glass matrix. These pores can be interconnected, allowing cell migration throughout the matrix. As surface area is inversely proportional to the diameter of the pore, the engineered implants maximize surface area for cell attachment by providing a desired surface-to-volume ratio of nano sized pores. The laws of physics suggest that these smaller pores are optimal for vascularization. Due to the osmotic pressure of the environment, a capillary effect will be observed with the nano and micro sized pores that results in biological fluid being wicked towards the center of the bioactive glass matrix. Likewise, the larger pores like the macro sized pores are optimal for oxygenation and nutrient exchange within the matrix.

After implantation, a calcium phosphate (CaP) layer forms around the construct. This calcium phosphate layer results from the chemical interaction of the bioactive glass material and the surrounding biological environment. At the same time, the smaller sized pores like the nano sized pores will be resorbing at a rate faster than the rest of the implant. As these nano sized pores resorb or become replaced with cells, they will bring in cellular activity and create a three-dimensional biostructure that, within itself, also has its own porosity. Thus, over time, new cells replace the resorbed material at a rate that maintains the mechanical integrity of the new construct. The new cells form their own network around the fibrous bioactive glass matrix, which fibers provide connectivity for the tissue growth. More importantly, because of the widespread distribution of nanopores throughout the fibrous matrix, the new cells are present in a density that makes the implant mechanically sound.

Unlike traditional bone graft scaffolds, the present bone graft implants offer both the necessary structure and function for clinical success, and allow the process of cell proliferation to occur in a non-uniform, multi-faceted fashion with the appropriate balanced rate of new cell proliferation replacing resorbed graft material. More importantly, this replacement occurs at select locations within the construct, without compromising overall mechanical integrity. In addition, the materials and implants allow this new tissue growth process to occur throughout the healing process, not just at the beginning of the process. The constant and simultaneous activities of cell proliferation and resorption occur throughout the entire healing time with the present bone graft materials and implants.

In some embodiments, the underlying bioactive material forming the foundation of the implant may be a bioactive glass. The bioactive glass may take the form of fibers, making them easy to handle in a clinical setting. Accordingly, in one embodiment, the engineered implant may be a fibrous scaffold formed of fibrous bioactive glass fibers. These fibers may be unrestricted, and allowed to move freely over one another. Alternatively, the fibers may be partially or fully fused to provide a more organized, rigid and structured network of fibers. Such a fibrous scaffold would allow for stimulation and induction of the natural biologic healing process found in fibrin clots whose mechanism is similar to that of new bone formation. One theory of the mechanism of action as provided by the fibrous nature of the scaffold is provided below.

The standard method for healing natural tissue with synthetic materials has been to provide a device having the microstructure and macrostructure of the desired end product. Where the desired end product is cancellous bone, traditional bone grafts have been engineered to mimic the architecture of cancellous bone. Although this has been the current standard for bone grafts, it does not take into account the fact that bone is a living tissue. Each bony trabeculae is constantly undergoing active biologic remodeling in response to load, stress and/or damage. In addition, cancellous and cortical bone can support a vast network of vasculature. This network not only delivers nutrients to sustain the living environment surrounding bone, but also supports red blood cells and marrow required for basic biologic function. Therefore, merely providing a synthetic material with the same architecture that is non-biologic is insufficient for optimal bone healing and bone health. Instead, what is required is a mechanism that can recreate the living structure of bone.

Traditional synthetics act as a cast, or template, for normal bone tissue to organize and form. Since these synthetics are not naturally occurring, eventually the casts or templates have to be resorbed to allow for normal bone to be developed. If these architectured synthetics do not resorb and do not allow proper bone healing, they simply become foreign bodies that are not only obstacles, but potentially detrimental, to bone healing. This phenomenon has been observed in many studies with slow resorbing or non-resorbing synthetics. Since these synthetics are just chemically inert, non-biologic structures that only resemble bone, they behave as a mechanical block to normal bone healing and development.

With the understanding that bone is a living biologic tissue and that inert structures will only impede bone healing, a different physiologic approach is presented with the present invention. Healing is a phasic process starting with some initial reaction. Each phase builds on the reaction that occurred in the prior phase. Only after a cascade of phases does the final development of the end product occur—new bone tissue. The traditional method has been to replace or somehow stimulate healing by placing an inert final product as a catalyst to the healing process. This premature act certainly does not account for the physiologic process of bone development and healing.

The physiologic process of bone healing can be broken down to three phases: (a) inflammation; (b) osteogenesis; and (c) remodeling. Inflammation is the first reaction to injury and a natural catalyst by providing the chemotactic factors that will initiate the healing process. Osteogenesis is the next phase where osteoblasts respond and start creating osteoid, the basic material of bone. Remodeling is the final phase in which osteoclasts and osteocytes then recreate the three-dimensional architecture of bone.

In a normal tissue repair process, at the initial phase a fibrin clot is made that provides a fibrous architecture for cells to adhere. This is the cornerstone of all connective tissue healing. It is this fibrous architecture that allows for direct cell attachment and connectivity between cells. Ultimately, the goal is to stimulate cell proliferation and osteogenesis in the early healing phase and then allow for physiologic remodeling to take place. Since the desired end product is living tissue, the primary objective is to stimulate as much living bone as possible by enhancing the natural fiber network involved in initiation and osteogenesis as well as angiogenesis.

Fibrous bone graft materials and bone graft implants formed from these fibrous materials have previously been disclosed in U.S. Patent Application Publication No. 2011/0144764 entitled "Bone Graft Material", U.S. Patent Application Publication No. 2011/0144763 entitled "Dynamic Bioactive Bone Graft Material Having an Engineered Porosity", and in U.S. Patent Application Publication No. 2011/0316 entitled "Dynamic Bioactive Bone Graft Material and Methods for Handling", all of which are co-pending and co-owned by applicants, the contents of which are incorporated herein by reference. These bone graft implants attempt to recapitulate the normal physiologic healing process by presenting the fibrous structure of the fibrin clot. Since these bioactive implants made of fibers are both osteoconductive as well as osteostimulative, the fibrous network will further enhance and accelerate bone induction. Further, the free-flowing nature of the bioactive fibrous matrix or scaffold allows for natural initiation and stimulation of bone formation rather than placing a rigid template that may impede final formation as with current graft materials. The fibers of the implants can also be engineered to provide a chemical reaction known to selectively stimulate osteoblast proliferation or other cellular phenotypes.

The present disclosure provides several embodiments of fibrous bone graft implants formed of bioactive glass fibers similar to those previously disclosed by applicants. The bundles of bioactive glass fibers are ultraporous, and include a combination of nano, micro, meso and macro pores. The fibrous nature of the material allows the bioactive glass fibers to be easily molded or shaped into clinically relevant shapes as needed for different surgical and anatomical applications, while maintaining the material's porosity. One manner of molding or shaping the scaffold is by placing the fibers into a mold tray, similar to the manner described in U.S. Patent Application Publication No. 2011/0316 entitled "Dynamic Bioactive Bone Graft Material and Methods for Handling". The implant may comprise bioactive glass fibers alone, or with additives as described above.

Another manner of shaping the implant is with the use of a jig. Due to the fibrous and pliable nature of the base material, it is also possible to add a biological fluid to the fibrous matrix and press into a formed shape with the fluid contained therein. Of course, it is understood that the fibrous material may just as easily be compressed in a mold. Liquids like bone marrow aspirate, glue or other binding agents may be added to the material prior to molding. In addition, a solvent exchange may be utilized and the shaped material can be allowed to dry or cure to form a hardened solid scaffold for implantation.

The implants may be provided in clinically relevant shapes. Simple shapes like cylinders or rods, or a strip, may be convenient for easy implantation. Alternatively, the implants may take the form of complex shapes to closely match the anatomy of the patient. For example, the implants may be formed in the shape of a shell, such as for instance an acetabulum shell. In another example, the material may be formed as a thin sheet or strip that is capable of being wrapped around the bone area to be treated, such as a bone defect site, much like a wound dressing. In that instance, the sheet or strip of material would not necessarily have to be inserted into the wound site, but rather cover the wound site while still providing the same benefits and acting in the same manner as the implants described herein.

The implants may be packaged in a clinically useful and friendly tray. The tray may be closed to control density and consequently dosage of the implant. The dosage may be dictated by the clinical application. It is also possible to use the tray as a mold, such that the shape of the tray creates a clinically relevant shaped implant. Another benefit of the tray is to allow fluids or liquids to be added to the implant. Such fluids may include saline, bone marrow, bone marrow concentrate, stem cells, platelet-rich plasma, etc. The closed tray also avoids contamination of the implant while it is in the operating room before implantation, as it minimizes the need for clinical handling before implantation, and is convenient for transport.

The fibers forming the engineered scaffold have a relatively small diameter, and in particular, a diameter in the range of about 500 nanometers to about 50 microns, or a diameter in the range of about 0.1 to about 100 microns. In one embodiment, the fiber diameter can be less than about 10 nanometers, and in another embodiment, the fiber diameter can be about 5 nanometers. In some embodiments, the fiber diameter can be in the range of about 0.5 to about 30 microns. In other embodiments, the fiber diameter can fall within the range of between about 2 to about 10 microns. In still another embodiment, the fiber diameter can fall within the range of between about 3 to about 4 microns.

The bioactive glass fibers may be manufactured having predetermined cross-sectional diameters as desired. In one example, the bone graft implant may be formed from a randomly oriented matrix of fibers of uniform diameters. Further, the bioactive glass fibers may be formed having varying diameters and/or cross-sectional shapes, and may even be drawn as hollow tubes. Additionally, the fibers may be meshed, woven, intertangled and the like for provision into a wide variety of shapes.

For example, a bioactive glass fiber implant can be manufactured such that each fiber is juxtaposed or out of alignment with the other fibers could result in a randomly oriented fibrous matrix appearance due to the large amount of empty space created by the random relationship of the individual glass fibers within the material. Such a manufacture enables an implant with an overall soft or pliable texture so as to permit the surgeon to manually form the implant into any desired overall shape to meet the surgical or anatomical requirements of a specific patient's surgical procedure. Such an implant also easily lends itself to incorporating additives randomly dispersed throughout the fibers, such as those previously described and including bioactive glass granules, antimicrobial fibers, particulate medicines, trace elements or metals such as copper, which is a highly angiogenic metal, strontium, magnesium, zinc, etc. mineralogical calcium sources, and the like. Further, the bioactive glass fibers may also be coated with organic acids (such as formic acid, hyaluronic acid, or the like), mineralogical calcium sources (such as tricalcium phosphate, hydroxyapatite, calcium carbonate, calcium hydroxide, calcium sulfate, or the like), antimicrobials, antivirals, vitamins, x-ray opacifiers, or other such materials.

The implant may be engineered with fibers having varying resorption rates. The resorption rate of a fiber is determined or controlled by, among other things, its material composition and by its diameter. The material composition may result in a slow reacting vs. faster reacting product. Similarly, smaller diameter fibers can resorb faster than larger diameter fibers. Also, the overall porosity of the material can affect resorption rate. Materials possessing a higher porosity mean there is less material for cells to remove. Conversely, materials possessing a lower porosity mean cells have to do more work, and resorption is slower. Accordingly, the implant may contain fibers that have the appropriate material composition as well as diameter for optimal performance. A combination of different fibers may be included in the implant in order to achieve the desired result. For instance, the implant may comprise a composite of two or more fibers of a different material, where the mean diameter of the fibers of each of the materials could be the same or different.

Equally as important as the material composition and diameter is the pore size distribution of the open porosity and in particular the surface area of the open porosity. The present bone graft implants provide not only an improved pore size distribution over other bone graft implants, but a higher surface area for the open pores. The larger surface area of the open porosity of the present implants drives faster resorption by body fluids, allowing the fluid better access to the pores.

Another manner of further enhancing the bioactive graft material of the present disclosure is to provide an additional layer or coating of polymer over the material in its individual fiber form or in its shaped fibrous cluster form. For example, biocompatible, bioabsorbable polymer or film-forming agents such as polycaprolactones (PCL), polyglycolic acid (PGA), poly-L-Lactic acid (PL-LA), polysulfones, polyolefins, polyvinyl alcohol (PVA), polyalkenoics, polyacrylic acids (PAA), PEG, PLGA, polyesters and the like are suitable materials for coating or binding the fibrous graft material of the present invention. The resultant product is strong, carveable, and compressible, and may still absorb blood. Other suitable materials also include artificial polymers selected from poly(anhydrides), poly(hydroxy acids), polyesters, poly(orthoesters), polycarbonates, poly(propylene fumerates), poly(caprolactones), polyamides, polyamino acids, polyacetals, polylactides, polyglycolides, polysulfones, poly(dioxanones), polyhydroxybutyrates, polyhydroxyvalyrates, poly(vinyl pyrrolidones), biodegradable polycyanoacrylates, biodegradable polyurethanes, polysaccharides, tyrosine-based polymers, poly(methyl vinyl ether), poly(maleic anhydride), poly(glyconates), polyphosphazines, poly(esteramides), polyketals, poly(orthocarbonates), poly(maleic acid), poly(alkylene oxalates), poly(alkylene succinates), poly(pyrrole), poly(aniline), poly(thiophene), polystyrene, non-biodegradable polyurethanes, polyureas, poly(ethylene vinyl acetate), polypropylene, polymethacrylate, polyethylene, poly(ethylene oxide), and co-polymers, adducts, and mixtures thereof. The material may be partially or fully water soluble.

Applying this feature to the fibrous graft material of the present disclosure, in one embodiment the individual fibers of the bioactive glass fiber material may be coated with such a biocompatible polymer. The coating itself would be sufficiently thin so as not to impede the advantages from the physical attributes and bioactive properties of the base material as described. In other words, the polymeric coated fibers would still retain pliability and allow the user to easily mold or form the fibrous material into the desired shape for implantation. Such a polymeric coating would further enhance the handling of the fibrous material while still allowing the underlying base material to be used in the same manner as previously described. The polymeric component would also provide a mechanism for graft containment, controlled resorption, and controlled bioactivity or cellular activity. This polymeric component may comprise a solid layer, a porous or perforated layer, or a mesh or woven layer of material having channels therein for exchange of nutrients, cells or other factors contained within.

In another embodiment, the fibrous graft material may be formed or shaped into an initial geometry and then coated with the biocompatible polymer. For example, the fibrous graft material may be formed into fibrous clusters as previously mentioned. These fibrous clusters can then be encapsulated in a biocompatible polymer. The resulting implant would have a fibrous BAG center surrounding which is a polymeric coating or shell.

In still another embodiment, the fibrous graft material can be formed into a flat sheet or strip. The biocompatible polymer may be wrapped around the sheet or strip, encasing the sheet or strip in an envelope-like fashion. The composite sheet or strip could be cut, folded, rolled, crumpled, or otherwise shaped into a desired geometry appropriate for clinical application.

In yet another embodiment, a combination of fibers and granules or clusters (either fibrous BAG or solid BAG) may be interspersed on a sheet of the biocompatible polymer. The fibers or granules may be randomly placed, or layered in an organized pattern on the sheet of polymer. For example, a section of the layer could contain fibers only, and an adjacent section could contain granules only. The sheet of polymer may then be folded onto itself, rolled into a cylinder, or crumpled into a ball. Alternatively, the fibers alone or with added BAG granules (either fibrous BAG or solid BAG) may be shaped into a disc, block, rod, or other uniform shape. The overlapping layers of BAG material and polymer would provide a controlled resorption and cellular activity profile along the depth of the composite implant. That is, the variation in location as well as the material of the composite relative to the implant as a whole allows the user to design an implant with an engineered porosity.

Another variation of this embodiment would encompass a composite implant in which the concentration of material is greater at one end of the implant than another, such that the controlled resorption and cellular activity profile along the length of the composite implant. This type of composite implant could be achieved by discretely placing the component materials onto a sheet of polymer, then rolling at an angle so that the material is non-uniformly distributed along the length of the rolled construct.

The biocompatible polymeric coating may be heat wrapped or heat shrunk around the underlying fibrous bone graft material. In addition, the biocompatible polymeric coating may be a mixture of polymer and other components. For example, it is contemplated that the polymeric coating can comprise 100% of a particular polymer, such as for instance, PLA. However, a mixture of 50% PLA and 50% PEG may also be utilized. Likewise, the coating may be formed of a polymer—BAG composition. In this case, the coating could comprise 50% polymer with the remaining 50% comprising BAG granules or fibers, for instance. Of course, it is understood that the percentage of an individual component may vary as so desired, and the percentages provided herein are merely exemplary for purposes of conveying the concept.

An alternative material suitable for binding or containing the fibrous graft material is collagen, which could be provided as a slurry and then hardened such as by freeze-drying. This collagen could be human-derived collagen or animal-derived collagen, for instance.

Additionally, it is contemplated that additional BAG granules, beads, spheres, etc. or individual fibers may be adhered to the polymeric coating in order to provide a surface enhancement for adherence to the implant site. These BAG granules or fibers would allow a better friction fit with the patient, serving as structural features. For example, added surface features may include fibers, granules, particulates, and the like that can be included in the coating to provide an exterior with bioactive anchorage points to attract cellular activity and improve adhesion of the implant in situ.

At the same time, these additional BAG granules or fibers also serve as bioactive features to allow for a differential mechanism of resorption and a more sophisticated bioactivity profile, since these BAG granules and fibers are themselves also capable of initiating bioactivity. The BAG granules or fibers may be used with or without additional coatings, such as with or without the additional polymer coating. Moreover, it is understood that part or all of the BAG fibers and materials may be sintered or unsintered in these applications.

The addition of the polymeric component to the base fiber graft material provides the benefit of allowing ease of handling, but also adds a layer of control to the resorption rate and bioactivity. It could easily be contemplated that the polymeric component in all of the embodiments previously described could be porous itself, thereby providing a composite implant having controlled fluid interactivity. The ability to provide separate layers of BAG within a single implant also renders depth control to the bioactivity, as well as controlled graft containment.

The embodiments of the present disclosure are not limited, however, to fibers alone. In other embodiments, the bioactive glass fibers that form the foundation of the implant may be substituted or supplemented with bioactive granules. These granules may be uniform or non-uniform in diameter, and may comprise a mixture of differently sized diameters of granules. In addition, the granules may be formed of the same type of bioactive glass material, or a mixture of different materials selected from the group of suitable materials previously mentioned. The granules may be solid or porous, and in some cases a mixture of both solid and porous granules may be used. Regardless, the engineered implant comprising the granular foundation should still provide the desired pore size distribution, which includes a range of porosities that includes macro, meso, micro and nano pores.

Like the fibers, at least some or all of the granules forming the engineered implant may be coated with a polymeric coating. The coating may be solid or porous. This coating could be provided on individual granules, or it could envelope a cluster or group of granules. In other embodiments, the coating could comprise collagen. For instance, the coating could be a solid collagen or a perforated collagen. Added surface features including fibers, granules, particulates, and the like can be included in the coating to provide an exterior with bioactive anchorage points to attract cellular activity and improve adhesion of the implant in situ.

In addition, some embodiments may include a mixture of both granular bioactive glass as the primary material with secondary bioactive glass fibers as the carrier material. In such cases, both the primary and secondary materials are active. The fibrous carrier would be able to resorb quickly to create a chemically rich environment for inducing new cellular activity. Moreover, the fibrous material would serve as select attachment or anchorage sites for bone forming cells.

In some embodiments, at least some or all of the engineered implant may be coated with a glass, glass-ceramic, or ceramic coating. The coating may be solid or porous, and provide for better handling of the fibrous bioactive glass material. In one embodiment, the coating may be a bioactive glass such as 45S5 or S53P4. In another embodiment, the coating may be partially or fully fused such as by an application of high heat to melt some of the fibrous material, creating a slightly hardened or fully fused shell of material. For instance, this fusing or hardening would lead to a semi-soft crust, while the full sintering would lead to a hard crust around some or all of the implant.

In still further embodiments, the implants may comprise a multi-layered composite of varying or alternating materials. For example, in one case a bioactive glass fiber or granule may be encased in a polymer as described above, and then further encased in a bioactive glass. This additional bioactive glass layer could be the same as, or different, than the underlying bioactive glass. The resultant construct would therefore have varying resorption rates as dictated by the different layers of materials.

In addition to providing a structurally sound implant and the appropriate materials and porosities and pore size gradient for cell proliferation, the present bone graft materials and implants may also provide cell signals. This can be accomplished by the incorporation of biological agents such as growth factors. These factors may be synthetic, recombinant, or allogenic, and can include, for example, stem cells, demineralized bone matrix (DBM), as well as other known cell signaling agents.

In some embodiments, the engineered implants may be also osteoconductive and/or osteostimulatory. By varying the diameter and chemical composition of the components used in the embodiments, the engineered implants may have differential activation (i.e., resorbability), which may facilitate advanced functions like drug delivery of such drugs as antibiotics, as an example. One manner of providing osteostimulative properties to the implant is to incorporate bone marrow into the fibrous matrix. The incorporation of the marrow would produce an osteostimulative implant that accelerates cell proliferation.

In other embodiments, the engineered implant may also include trace elements or metals such as copper, zinc, strontium, magnesium, zinc, fluoride, mineralogical calcium sources, and the like. These trace elements provide selective benefits to the engineered structural and functioning implants of the present disclosure. For example, the addition of these trace elements like strontium may increase x-ray opacity, while the addition of copper provides particularly effective angiogenic characteristics to the implant. The materials may also be coated with organic acids (such as formic acid, hyaluronic acid, or the like), mineralogical calcium sources (such as tricalcium phosphate, hydroxyapatite, calcium sulfate, calcium carbonate, calcium hydroxide, or the like), antimicrobials, antivirals, vitamins, x-ray opacifiers, or other such materials. These bone graft materials may also possess antimicrobial properties as well as allow for drug delivery. For example, sodium or silver may be added to provide antimicrobial features. In one embodiment, a layer or coating of silver may be provided around the engineered implant to provide an immediate antimicrobial benefit over an extensive surface area of the implant. Other suitable metals that could be added include gold, platinum, indium, rhodium, and palladium. These metals may be in the form of nanoparticles that can resorb over time.

Additionally, biological agents may be added to the engineered implant. These biological agents may comprise bone morphogenic protein (BMP), a peptide, a bone growth factor such as platelet derived growth factor (PDGF), vascular endothelial growth factor (VEGF), insulin derived growth factor (IDGF), a keratinocyte derived growth factor (KDGF), or a fibroblast derived growth factor (FDGF), stem cells, bone marrow, and platelet rich plasma (PRP), to name a few. Other medicines may be incorporated into the scaffold as well, such as in granular or fiber form.

In general, the present disclosure provides bone graft materials and implants formed from these materials that are engineered with a combination of structural and functional features that act in synergy to allow the bone graft implant to support cell proliferation and new tissue growth over time. The implants provide the necessary porosity, pore size distribution and high surface area to allow proper vascularization, optimized cell attachment, migration, proliferation, and differentiation. The implants are formed of synthetic materials that are biocompatible and offer the requisite mechanical integrity to support continued cell proliferation throughout the healing process. These implants may comprise a fibrous or granular infrastructure of porous material that may be encased in bioactive material or polymer. In addition, these implants incorporate allograft material in the form of bone chips, stem-cell preserved bone chips, or human-derived collagen.

Embodiments of the present disclosure may be explained and illustrated with reference to the drawings. It should be understood, however, that the drawings are not drawn to scale, and are not intended to represent absolute dimensions or relative size. Rather, the drawings help to illustrate the concepts described herein.

Turning now to the drawings, FIG. 1A represents an exemplary embodiment of an engineered implant 10 that may be formed of fibrous bioactive glass material 20 having incorporated therein allograft material 60. The fibrous matrix may comprise free-flowing, randomly oriented fibers 20. As shown, the allograft material 60 may be concentrated in a discrete pocket of the implant 10, such as in the center or middle of the implant 10.

Figure 1B:
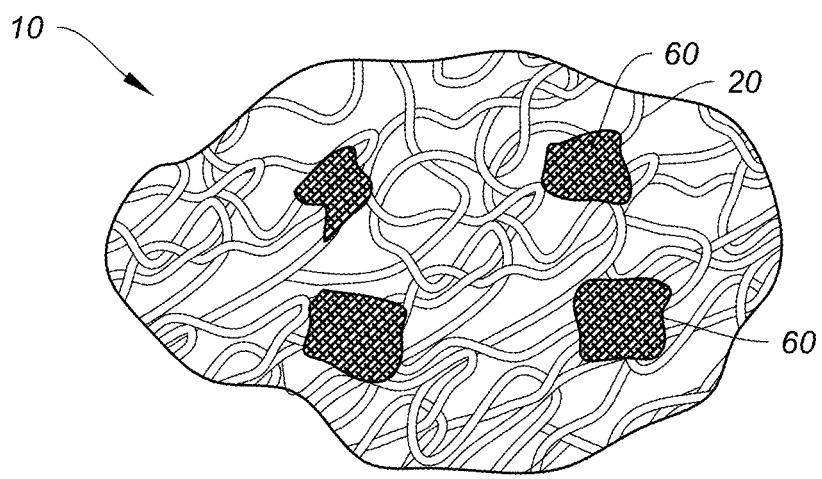
FIG. 1B illustrates a partial cutaway view of an exemplary embodiment of a bone graft implant of the present disclosure in which the implant comprises a fibrous matrix containing allograft fragments randomly dispersed throughout.

FIG. 1B represents an exemplary embodiment of an engineered implant 10 that may be formed of fibrous bioactive glass material 20 having incorporated therein allograft material 60. However, unlike in FIG. 1A, the allograft material 60 may be provided in small fragments or chips, and uniformly dispersed or spread out over the entirety of the implant 10.

Figure 2A:
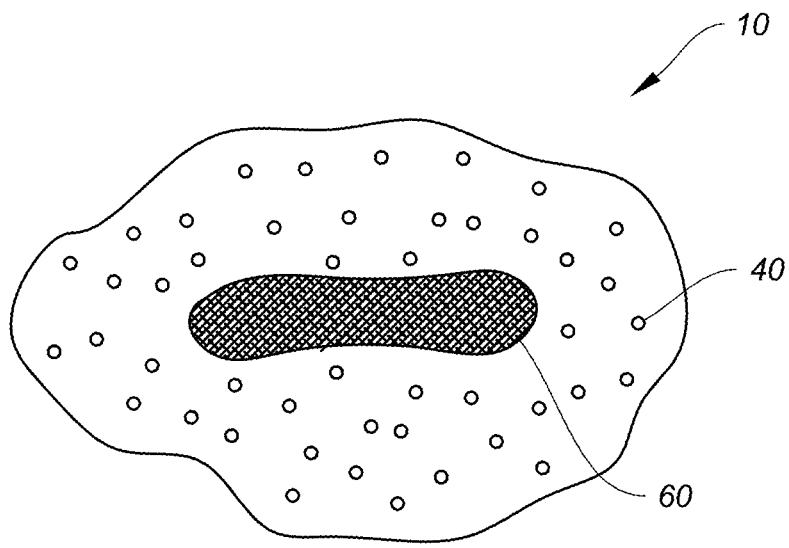
FIG. 2A illustrates a partial cutaway view of an exemplary embodiment of a bone graft implant of the present disclosure in which the implant comprises a granular matrix containing allograft.

FIG. 2A represents an exemplary embodiment of an engineered implant 10 that may be formed of granular bioactive glass material 40 having incorporated therein allograft material 60. As shown, the allograft material 60 may be concentrated in a discrete pocket of the implant 10, such as in the center or middle of the implant 10. In all instances, the implant may be further coated. An optional carrier may also be provided, such as collagen.

Figure 2B:
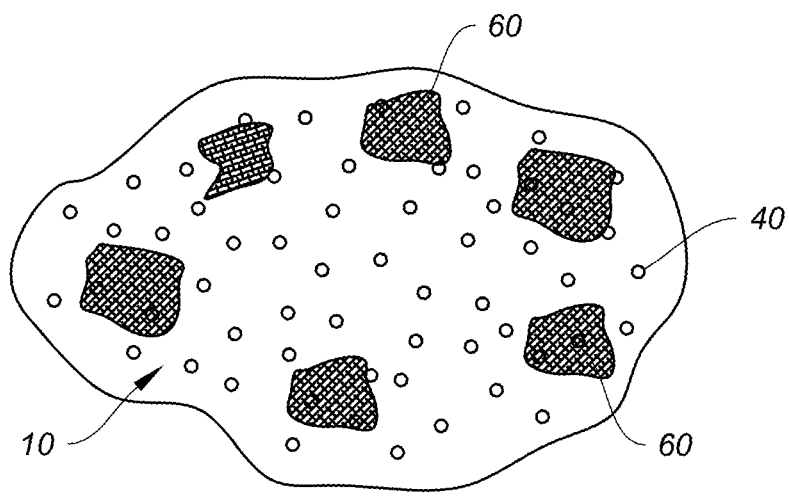
FIG. 2B illustrates a partial cutaway view of an exemplary embodiment of a bone graft implant of the present disclosure in which the implant comprises a granular matrix containing allograft fragments discretely dispersed throughout.

FIG. 2B represents an exemplary embodiment of an engineered implant 10 that may be formed of granular bioactive glass material 40 having incorporated therein allograft material 60. However, unlike in FIG. 2A, the allograft material 60 may be provided in small fragments or chips, and discretely placed in specific locations within the implant 10. For example, as shown, the allograft fragments 60 may be placed near an outer surface of the implant 10 to provide concentrated activity at the outer surface.

Figure 3:
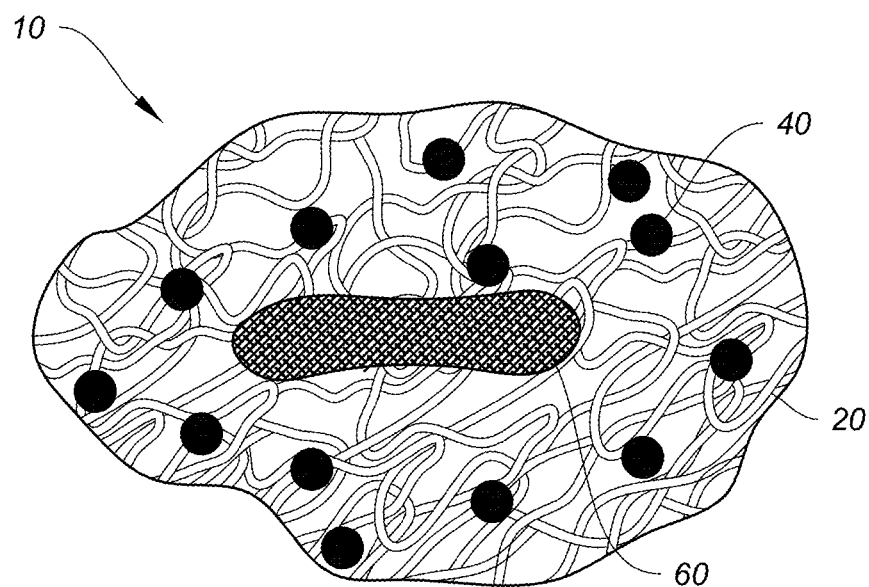
FIG. 3 illustrates a partial cutaway view of an exemplary embodiment of a bone graft implant of the present disclosure in which the implant comprises a fibrous matrix with granules and allograft.

FIG. 3 represents an exemplary embodiment of an engineered implant 10 that may comprise granules 40 in combination with fibers 20 having incorporated therein allograft material. In some cases, the fibers may be of varying bioactive glass materials. As shown, the allograft material 60 may be concentrated in a discrete pocket of the implant 10, such as in the center or middle of the implant 10. Optionally, the allograft material may be in the form of demineralized bone matrix (DBM), though bone chips may also be substituted for, or supplement, the DBM.

Figure 4A:
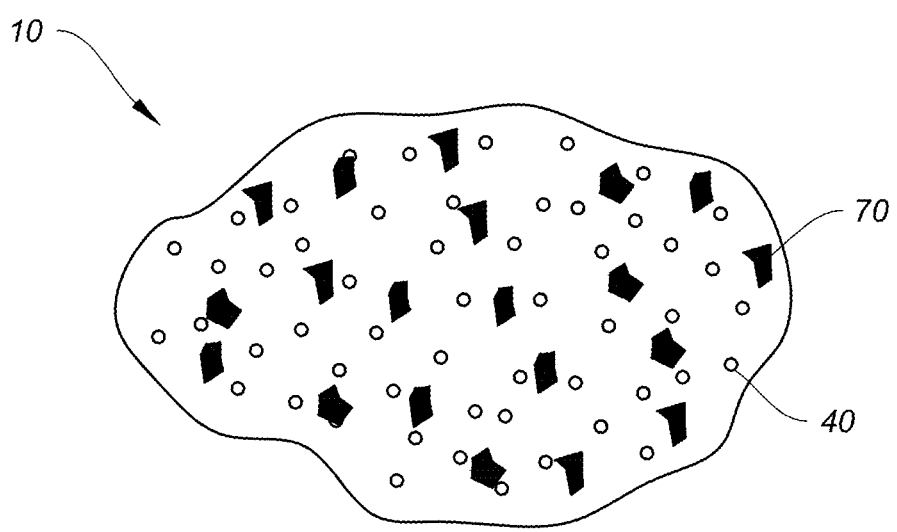
FIG. 4A illustrates a partial cutaway view of an exemplary embodiment of a bone graft implant of the present disclosure in which the implant comprises a granular matrix containing bone chips.
Figure 4B:
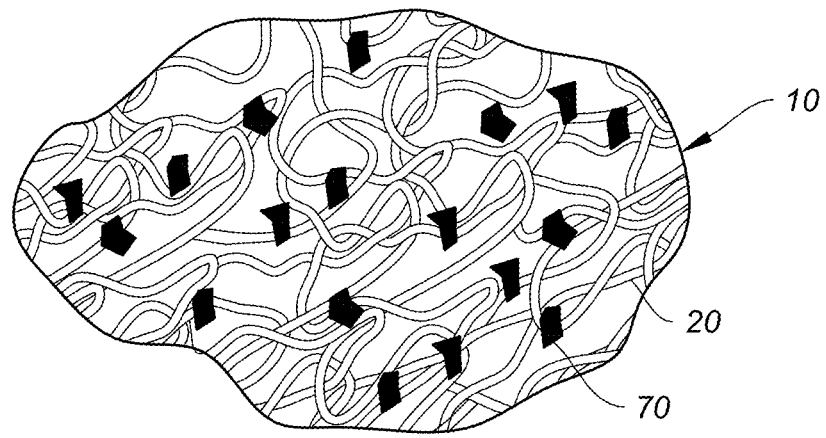
FIG. 4B illustrates a partial cutaway view of an exemplary embodiment of a bone graft implant of the present disclosure in which the implant comprises a fibrous matrix containing bone chips.
Figure 4C:
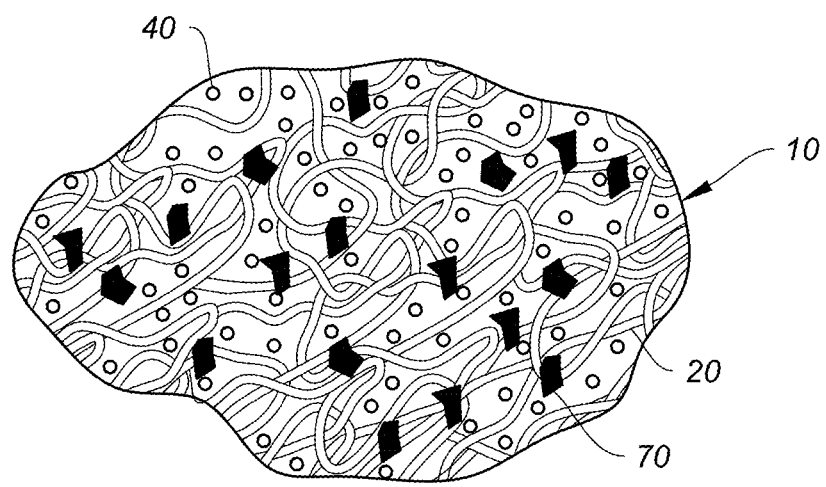
FIG. 4C illustrates a partial cutaway view of an exemplary embodiment of a bone graft implant of the present disclosure in which the implant comprises a fibrous and granular matrix containing bone chips.

FIG. 4A represents an exemplary embodiment of an engineered implant 10 having incorporated therein bone chips 70 with bioactive glass granules 40. FIG. 4B represents an exemplary embodiment of an engineered implant 10 having incorporated therein bone chips 70 with bioactive glass fibers 20. FIG. 4C represents an exemplary embodiment of an engineered implant 10 having incorporated therein bone chips 70 with both fibers 20 and granules 40.

The presence of granular matter may be employed to modify or control the resorption rate and resorption profile of the implant 10 as well as provide mechanical strength and compression resistance. The granules may be bioactive glass, calcium sulfate, calcium carbonate, calcium hydride, calcium phosphate, or hydroxyapatite. The granule may be solid, or it may be porous. These granules may serves as anchors for cell attachment, spacers between fibers to control distribution and dosage, or carry biological agents to provide antimicrobial properties or osteostimulative agents.

As shown, these bone chips may be evenly distributed throughout the implant 10. Alternatively, the bone chips 70 may be concentrated in discrete pockets. In addition, the diameters of each of the materials may also vary so as to produce an engineered implant that is selectively composed and structured to have differential or staged resorption capacity. As previously mentioned, these fibers may be individual coated, or the entire fibrous implant along with the allograft material may be coated.

In other embodiments, the allograft material may comprise demineralized bone matrix rather than bone chips. Furthermore, the implant may comprise one or more different glass materials to vary the composition of the implant. Additional biological agents and additives such as those previously mentioned may be utilized.

Figure 5A:
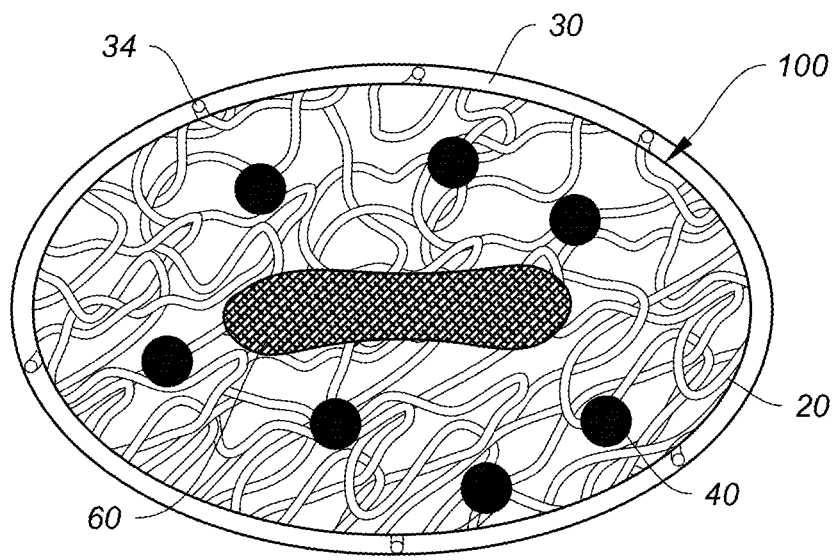
FIG. 5A illustrates a partial cutaway view of an exemplary embodiment of a bone graft implant of the present disclosure in which the implant comprises a fibrous matrix containing granules and allograft and encased in a polymeric shell.
Figure 5B:
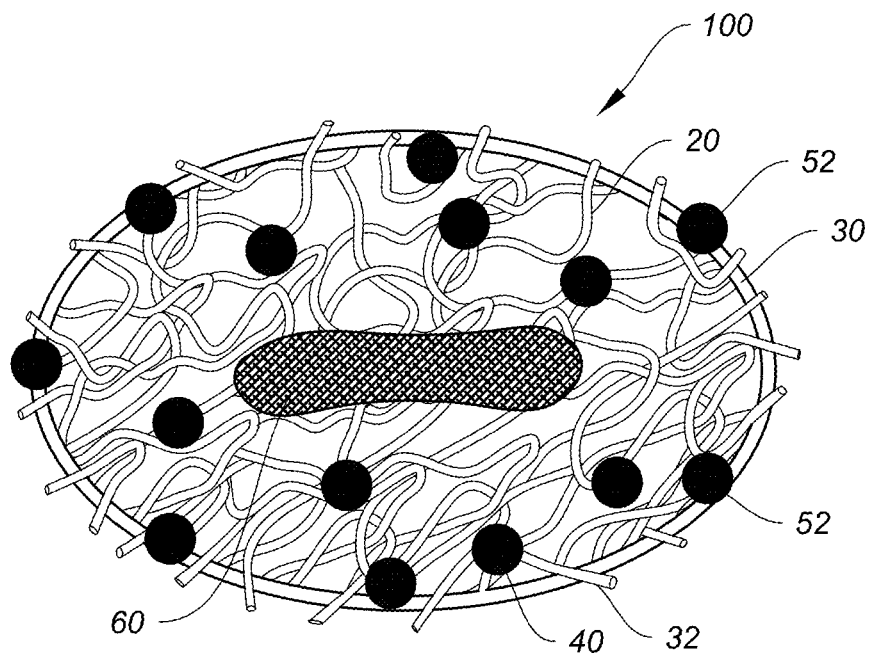
FIG. 5B illustrates a partial cutaway view of an exemplary embodiment of a bone graft implant of the present disclosure in which the implant comprises a fibrous matrix containing granules and allograft and encased in a polymeric shell with surface features.

It is contemplated that the fibers and/or granules may further include a polymeric coating, as shown in FIGS. 5A and 5B. The coating 30 may be porous 34, and provide for better handling of the fibrous bioactive glass material. These pores or vents 34 allow free migration of cells and nutrients within the internal fibrous matrix, thereby improving the healing process. The underlying implant may be sintered or not, as mentioned above. The coating may be selectively placed over the fibers only, the granules only, or on both or some portion of each.

The inclusion of bioactive glass granules can be accomplished using granules having a wide range of sizes or configurations to include roughened surfaces, very large surface areas, and the like. For example, granules may be tailored to include interior lumens with perforations to permit exposure of the surface of the granule's interior. Such granules would be more quickly absorbed, allowing a tailored material characterized by differential resorbability. The perforated or porous granules could be characterized by uniform diameters or uniform perforation sizes, for example. The porosity provided by the granules may be viewed as a secondary range of porosity accorded the bone graft material or the implant formed from the bone graft material. By varying the size, transverse diameter, surface texture, and configurations of the bioactive glass fibers and granules, if included, the manufacturer has the ability to provide a bioactive glass bone graft material with selectively variable characteristics that can greatly affect the function of the material before and after it is implanted in a patient. The nano and micro sized pores provide superb fluid soak and hold capacity, which enhances the bioactivity and accordingly the repair process.

Accordingly, the engineered implant can be selectively determined by controlling compositional and manufacturing variables, such as bioactive glass fiber diameter, size, shape, and surface characteristics as well as the amount of bioactive glass granular content and structural characteristics, and the inclusion of additional additives, such as, for example tricalcium phosphate, hydroxyapatite, and the like. By selectively controlling such manufacturing variables, it is possible to provide an artificial bone graft material having selectable degrees of characteristics such as porosity, bioabsorbability, tissue and/or cell penetration, calcium bioavailability, flexibility, strength, compressibility and the like.

It is contemplated that in some embodiments, either fibers or granules, or a combination of both, may be added to the coating. The fibers 32 or granules 52, which themselves may or may not be coated, would extend beyond the outer surface of the scaffold, providing a surface feature that enhances adhesion and creates a cell attachment surface. FIG. 5B illustrates this concept, showing a combination of fibers 20 and granules of bioactive glass 40 along with allograft material 60, all contained within a polymeric coating 30. This coating could be sealed, as shown.

One of the benefits of providing an ultra-porous bioactive glass material in granular form is that handling of the material can be improved. In one manner of handling the granular material, the granules may be packaged in a syringe with a carrier, and injected into the bone defect with ease. Another benefit is the additional structural effect of having a plurality of clusters closely packed together, forming additional macrostructures to the overall implant of material. Like a sieve, the openings between individual clusters can be beneficial such as when a filter is desired for various nutrients in blood or bone marrow to concentrate certain desired nutrients at the implant location.

Another implant useful for clinical applications is a kneadable, conformable, or otherwise moldable formulation or putty. Putty implants are desirable because the putty can be applied directly to the injury site by either injection or by plastering. Putty implants are also easy to handle and moldable, allowing the clinician the flexibility to form the material easily and quickly into any desired shape. In addition, the putty possesses the attributes of malleability, smearability, and injectability.

Accordingly, the bioactive glass material may be mixed with a carrier material for better clinical handling, such as to make a putty or foam implant. A pliable implant in the form of a putty may be provided by mixing the bioactive glass material with a flowable or viscous carrier. A foam implant may be provided by embedding the bioactive glass material in a porous matrix such as collagen (either human or animal derived) or porous polymer matrix. One of the advantages of a foam implant is that the porous carrier can also act as a site for attaching cells and growth factors, and may lead to a better managed healing.

The carrier material may be porous and may help contribute to healing. For example, the carrier material may have the appropriate porosity to create a capillary effect to bring in cells and/or nutrients to the implantation site, similar to the benefits that the fibers provide. The carrier material may also possess the chemistry to create osmotic or swelling pressure to bring in nutrients to the site and resorb quickly in the process. For instance, the carrier material may be a polyethylene glycol (PEG) which has a high affinity to water.

In one embodiment, the putty may have a more fluid than kneadable consistency to allow to be easily injected from a syringe or other injection system. This could be very useful in a minimally invasive system where you want as little disruption to the damaged site and to the patient as possible. For instance, a treatment may involve simply injecting the flowable putty of material into the area of bone damage using a syringe, cannula, injection needle, delivery screw, or other medical delivery portal for dispersal of injectable materials. This treatment may be surgical or non-surgical.

The combination of the ultra-porous fibrous clusters formed of bioactive glass, combined with porous bioactive glass granules and a carrier material, forms an improved putty implant over currently available putties. In one embodiment, the putty may comprise fibers and fiber clusters in a carrier material. In another embodiment, the putty may comprise fibrous clusters as previously mentioned, bioactive glass granules, and the carrier material, the fibers and granules being polymerically coated as described above. The sintered fibrous clusters as well as the bioactive glass granules may be porous, where each component may have a range or gradient of porosities throughout. The combination thus provides the putty with variable resorption rates. As mentioned above, these fiber and glass clusters may be engineered with variable porosities, allowing the customization of the putty formulation. In some embodiments, the putty includes any combination of nanopores, macropores, mesopores, and micropores.

The carrier material for the putty implant can be phospholipids, carboxylmethylcellulose (CMC), glycerin, polyethylene glycol (PEG), polylactic acid (PLA), polylactic-co-glycolic acid (PLGA), or other copolymers of the same family. Other suitable materials may include hyaluronic acid, or sodium alginate, for instance. The carrier material may be either water-based or non-water based, and may be viscous. Another carrier material alternative is saline or bone marrow aspirate, to provide a stickiness to the implant. Additives such as those described above, such as for example, silver or another antimicrobial component, may also be added to provide additional biological enhancements.

In other embodiments, the collagen may be a fully or partially water soluble form of collagen to allow the collagen to soften with the addition of fluids. In still other embodiments, the collagen may a combination of soluble and fibrous collagen. The collagen may be human derived collagen, in some instances, or animal derived collagen.

The use of sintered fiber clusters may be advantageous in some instances, because the sintering provides relative hardness to the clusters, thereby rendering the sintered clusters mechanical stronger. Their combination with the glass granules further enhances the structural integrity, mechanical strength, and durability of the implant. Because larger sized granules or clusters will tend to have longer resorption time, in previous cases the user had to sacrifice strength for speed. However, as applicants have discovered, it is possible to provide larger sized granules or clusters to achieve mechanical strength, without sacrificing the speed of resorption. To this end, ultra-porous clusters may be utilized. Rather than using solid spheres or clusters, ultra-porous clusters that have the integrity that overall larger sized clusters provide, along with the porosity that allows for speed in resorption, can be used. These ultra-porous clusters will tend to absorb more nutrients, resorb quicker, and lead to much faster healing and remodeling of the defect.

It is contemplated that the putty could be formulated for injectable delivery. For example, one manner in which to apply the putty would include a syringe containing the bioactive material that can be opened to suction into the syringe the necessary fluid to form the putty, while the same syringe can also be used to inject the as-formed putty implant. In other examples, a syringe with threaded attachments such as a removable cap may be utilized for site-specific delivery.

The use of sintered fiber clusters may be advantageous in some instances, because the sintering provides relative hardness to the clusters, thereby rendering the sintered clusters mechanical stronger. Their combination with the glass granules further enhances the structural integrity, mechanical strength, and durability of the implant. Because larger sized granules or clusters will tend to have longer resorption time, in previous cases the user had to sacrifice strength for speed. However, as applicants have discovered, it is possible to provide larger sized granules or clusters to achieve mechanical strength, without sacrificing the speed of resorption. To this end, ultra-porous clusters may be utilized. Rather than using solid spheres or clusters, ultra-porous clusters that have the integrity that overall larger sized clusters provide, along with the porosity that allows for speed in resorption, can be used. These ultra-porous clusters will tend to absorb more nutrients, resorb quicker, and lead to much faster healing and remodeling of the defect.

In some embodiments, an engineered implant comprising fibers formed into a cluster in the manner previously described, along with unsintered fibers of a different material may be provided. The unsintered fibers would serve as the carrier for the fibrous clusters. A putty implant could be formed by adding saline or blood marrow aspirate, to provide a stickiness to the implant. Thus the putty could include two different bioactive glass materials.

In still another embodiment, the graft material may be provided in the form of a foam. For example, the addition of collagen to the base graft material would produce a foam implant that could be shaped into strips, sheets, or cylindrical rolls. These strips, sheets, or rolls could then be easily cut, folded, or otherwise formed into the ultimate geometry of the implant. In addition, these sheets may serve as a wound dressing or wrap around the bone defect site for healing.

As previously mentioned, the fiber clusters may be sintered to provide hard clusters. Of course, it is contemplated that a combination of both sintered fiber clusters (hard granules) and unsintered clusters (soft granules) may be used in one application simultaneously. Likewise the combination of putty, foam, and clusters as described herein may be used in a single application to create an even more sophisticated porosity gradient and ultimately offer a better healing response. In some cases, solid porous clusters of the bioactive glass material may also be incorporated into the composition.

Additionally, these fibrous clusters may be encased or coated with a polymer. The coating material itself may be porous. Thus, a fibrous cluster may be further protected with a coating formed of polymer. The advantage of coating these fibrous clusters is to provide better handling since highly porous materials tend to have low strength, are prone to breakage and can become entangled. The addition of a coating having the same properties as the underlying fibrous foundation would therefore create a bead-like composition that offer yet another layer of protection as well as an additional porosity gradient.

It is contemplated that various compositions and formulations of the invention of the present disclosure can be achieved through combinations of the major components of the bioactive glass implant and polymeric containment layer as described. For example, one combination can include a single material of either fibrous or granular bioactive material laid onto a polymeric base layer, which can then be rolled into a cylindrical shape and delivered to an implantation site. Alternatively, after being rolled, the implant may be shaped or cut as desired and then inserted into the site. If so desired, the roll may be sealed.

Of course, it is understood that multiple layers of materials may be applied, either as discrete layers or as a mixture, depending on the number of layers desired. In addition, a composite of multiple layers of the polymeric base with layers of the material, either in discrete sections on a single layer or as an entire layer itself, can be envisioned whereby the materials create a stacking effect to form a block of bone graft material.

FIGS. 6A, 6B, 7A, and 7B illustrate combinations in which a plurality of materials of either fibrous or granular bioactive material are laid onto a polymeric base layer, along with an allograft component, which can then be rolled into a cylindrical shape and delivered to an implantation site. Alternatively, after being rolled, the implant may be shaped or cut as desired and then inserted into the site. If so desired, the roll may be sealed. Additional other agents or components may also be added, such as those previously described like the antimicrobial agents.

Figure 6A:
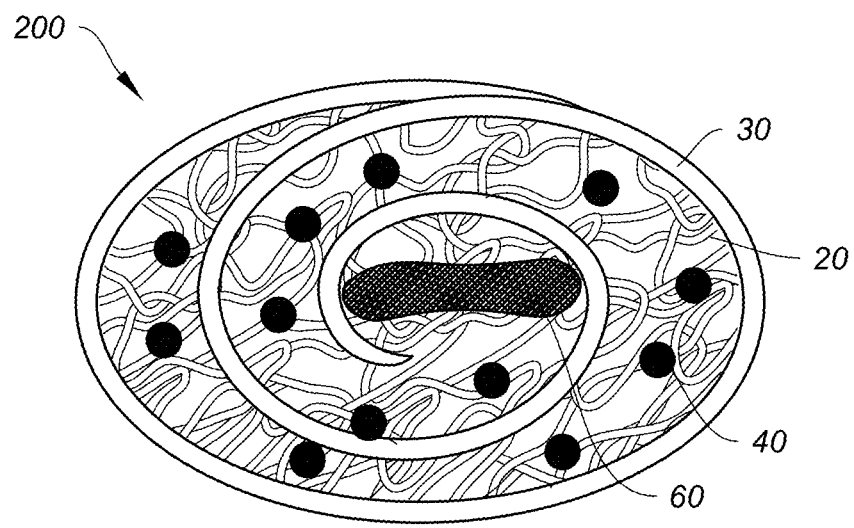
FIG. 6A illustrates a perspective view of another exemplary embodiment of a composite bone graft implant of the present disclosure in which the implant comprises a fibrous matrix with granules and allograft, and encased in a polymeric coating.
Figure 6B:
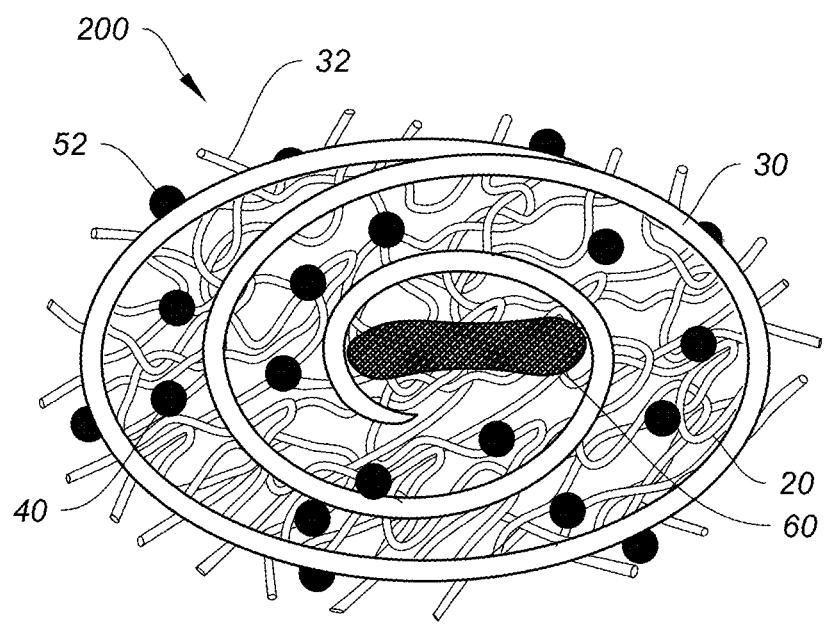
FIG. 6B illustrates a perspective view of another exemplary embodiment of a composite bone graft implant of the present disclosure in which the implant comprises a fibrous matrix with granules and allograft, and encased in a polymeric coating with surface features.

As shown, the materials may be discretely laid in a prearranged order so that a material may be concentrated on the interior of the roll, such as in FIGS. 6A and 6B, while a different material may be concentrated near the exterior of the roll. In other words, the materials may be selectively concentrated in discrete pockets depending on the arrangement of the material on the polymeric base layer. This type of discrete arrangement of the materials results in a layering effect of the graft materials. In the case of FIGS. 6A and 6B, the composite implant 200 comprises a matrix of fibers 20 and granules 40 surrounding a core of allograft material 60 which resides within the core of the implant 200. As the rolled implant 200 is sealed at the edge, a cylindrical or rod-shaped implant 200 is produced.

As FIG. 6B illustrates, the implant 200 may also include surface features like granules 52 or short wavy fibers 32. These added surface features be included in the coating 30 to provide an exterior with bioactive anchorage points to attract cellular activity and improve adhesion of the implant in situ.

Figure 7A:
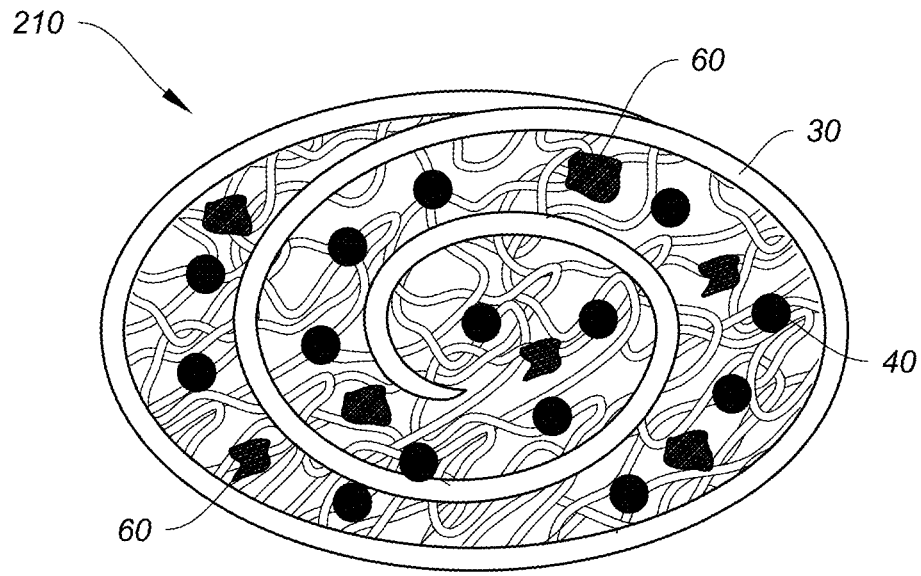
FIG. 7A illustrates a perspective view of another exemplary embodiment of a composite bone graft implant of the present disclosure in which the implant comprises a fibrous matrix with granules and randomly dispersed allograft fragments, and encased in a polymeric coating.
Figure 7B:
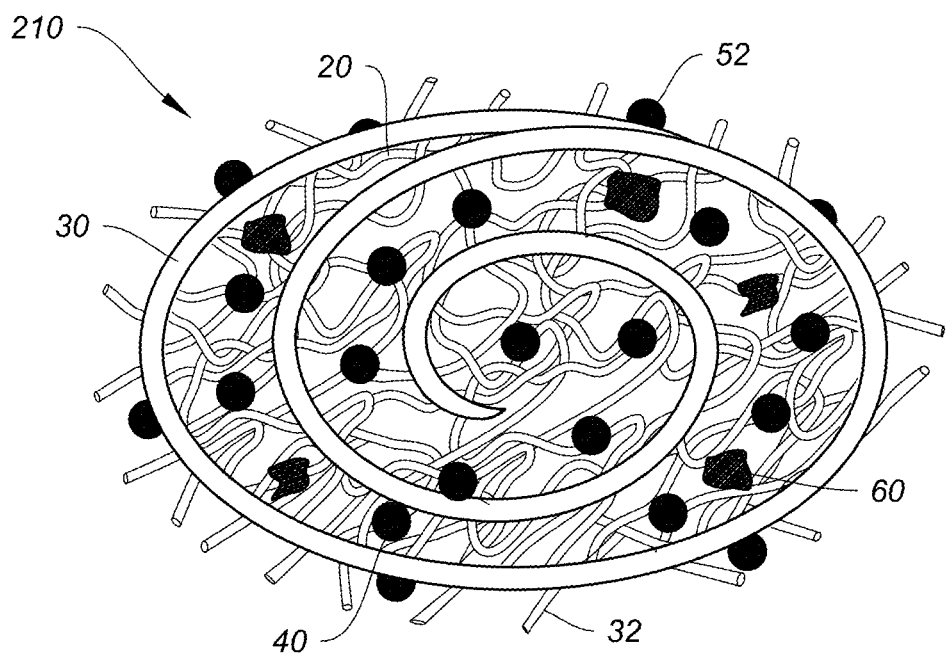
FIG. 7B illustrates a perspective view of another exemplary embodiment of a composite bone graft implant of the present disclosure in which the implant comprises a fibrous matrix with granules and randomly dispersed allograft fragments, and encased in a polymeric coating with surface features.

FIGS. 7A and 7B represent an exemplary embodiment of a composite implant 210 that comprises a matrix of fibers 20 and granules 40 surrounding a plurality of allograft fragments 60 that are randomly dispersed throughout the implant 200. As the rolled implant 200 is sealed at the edge, a cylindrical or rod-shaped implant 210 is produced.

As FIG. 7B illustrates, the implant 210 may also include surface features like granules 52 or short wavy fibers 32. These added surface features can be included in the coating 30 to provide an exterior with bioactive anchorage points to attract cellular activity and improve adhesion of the implant in s It is of course understood that the allograft fragments 60 may also be discretely laid onto the polymer sheet 30 prior to assembly, such that the allograft fragments 60 are concentrated at a discrete pocket within the implant 210, or in such a configuration that the allograft fragments 60 are concentrated on a discrete layer of the multi-layer rolled composite implant 210.

Figure 8:
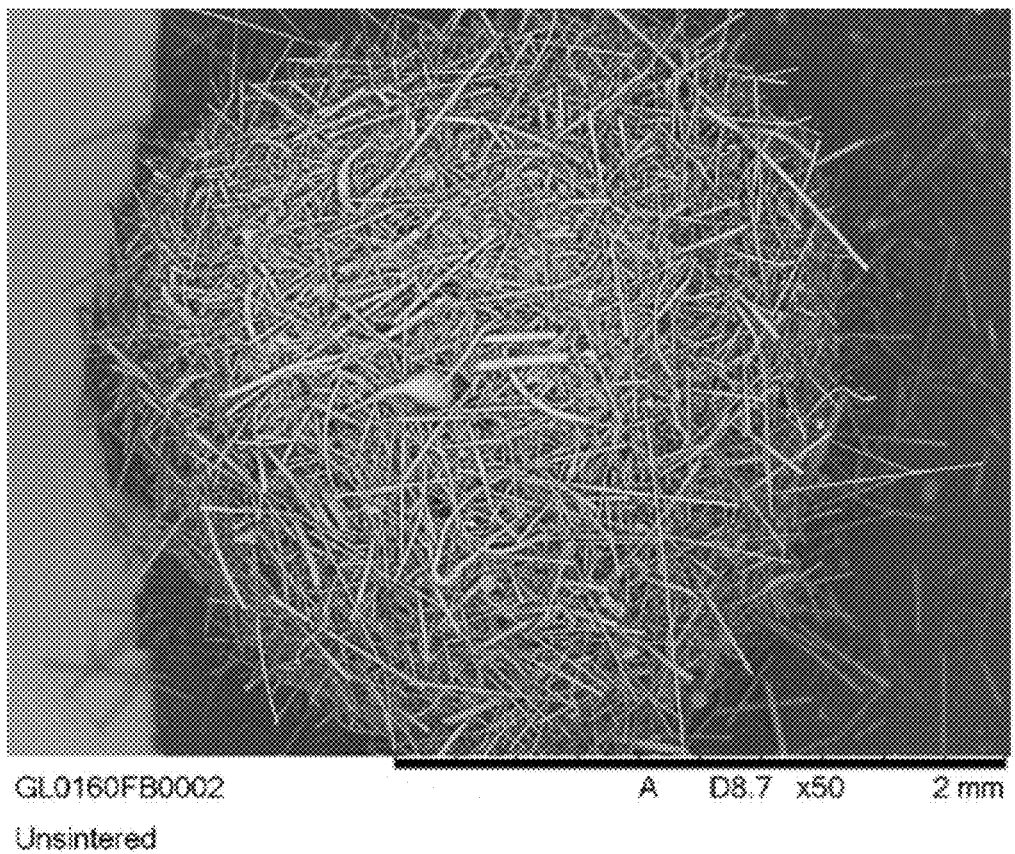
FIG. 8 shows a scanning electron micrograph (SEM) of a fibrous bioactive glass implant of the present disclosure.
Figure 9:
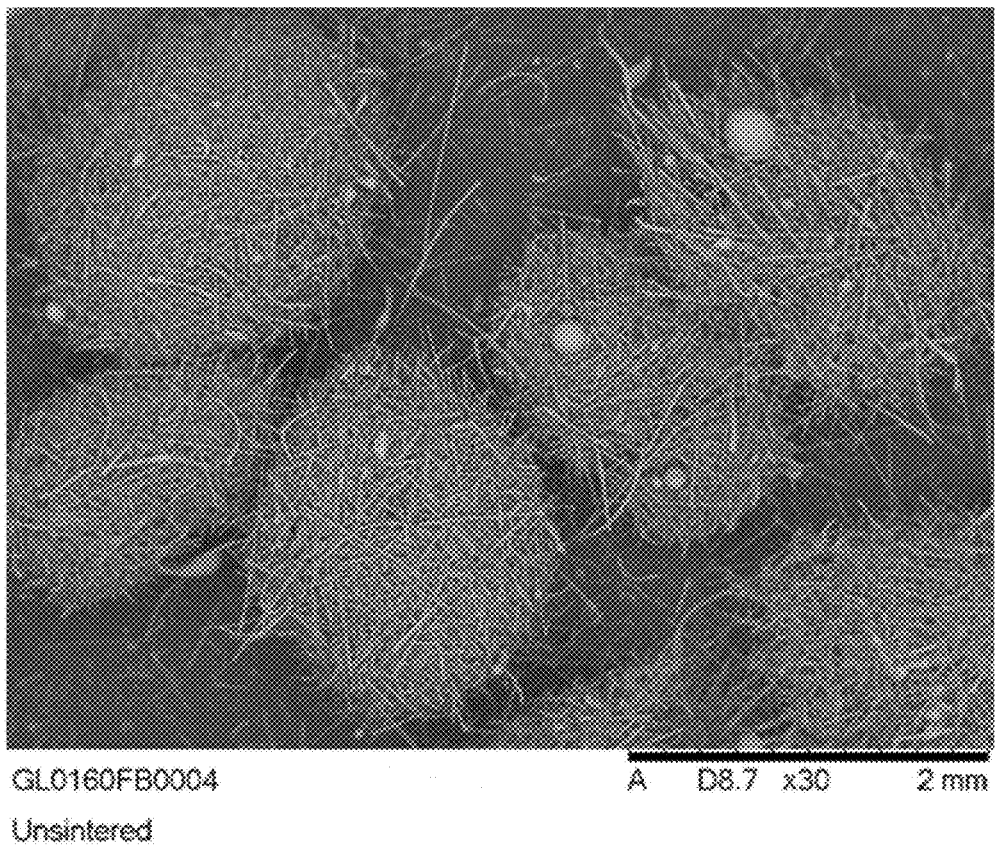
FIG. 9 shows a scanning electron micrograph (SEM) of a bioactive glass implant of the present disclosure comprising a fibrous matrix with granules.

As shown in the scanning electron micrographs of FIGS. 8 to 11, the fibrous matrix of the implant may take the form of a cluster, such as shown in FIG. 8, whereby the fibrous architecture of the implant is evident. This fibrous architecture provides the implant with a structure that mimics the structure of a human fibrin clot. Granules may be incorporated into the fibrous matrix, and such granules may extend out of the exterior of the implant, as shown in FIG. 9.

Figure 10:
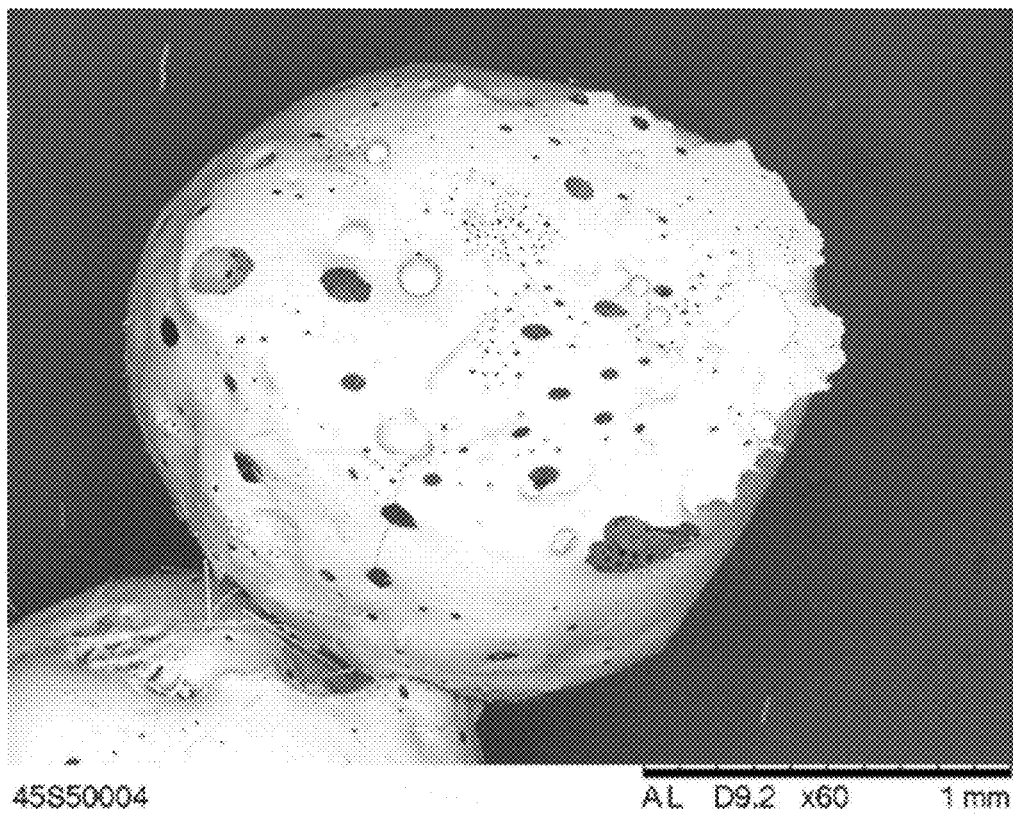
FIG. 10 shows a scanning electron micrograph (SEM) of a fibrous cluster of the present disclosure.
Figure 11:
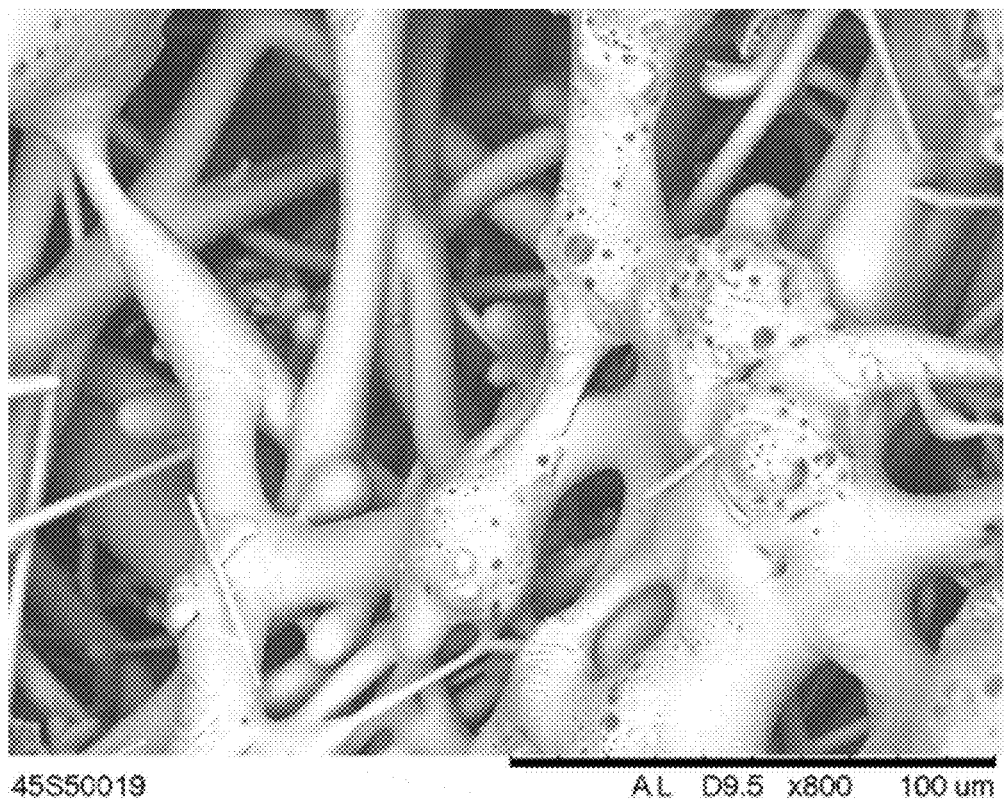
FIG. 11 shows a scanning electron micrograph (SEM) of the fibrous matrix within the cluster of FIG. 10.

FIG. 10 shows a fibrous granule having a partially hardened shell. This shell is also porous to allow cell and nutrient exchange. As shown in greater detail in FIG. 11, individual fibers within the fibrous matrix of the granule are also porous.

In some embodiments, the fiber diameter may be in the range of about about 0.1 to about 100 microns. In other embodiments, the diameter can be the range of about 0.5 to about 30 microns. In still other embodiments, the diameter can be less than about 10 microns. In one embodiment, the fiber diameter can fall within the range of between about 2 to about 10 microns.

In some embodiments, the fiber clusters may have a diameter in the range of about 0.75 to about 4.0 mm. In other embodiments, the fiber clusters may have a diameter in the range of about 2.0 to about 4.0 mm.

In some embodiments, the glass granules may have a diameter in the range of about 1 to 5 mm, or about 950 microns to about 3 mm, or about 850 microns to about 3 mm. In other embodiments, the glass granules may have a diameter in the range of about 50 to 450 microns, or about 150 to 450 microns.

Although the engineered implant of the present disclosure is described for use in bone grafting, it is contemplated that the implant of the present disclosure may also be applied to soft tissue or cartilage repair as well. Accordingly, the application of the implant provided herein may include many different medical uses, and especially where new connective tissue formation is desired. One such clinical application is in the area of nucleus replacement, where the engineered implant could be inserted into the disc nucleus as part of a nucleus replacement therapy. Another suitable clinical application is for large bone defects or lesions, particularly with the addition of platelet rich plasma (PRP) to the implant composition. Even still, the implant may be applied as a bone filler such as a replacement or substitute for bone cement in bone defect repairs. A silane coating may be applied over the implant to make it more suitable in that capacity.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A porous, composite bone graft implant comprising:
    a first component comprising a bioactive glass material in the form of a plurality of bioactive glass clusters, each cluster comprising a matrix of randomly oriented bioactive glass fibers and bioactive glass granules, at least some of the fibers and granules being sintered together, the clusters further including a bioactive glass shell at least partially encasing the matrix;
    a second component comprising an allograft material, the second component being interspersed with the first component throughout the composite bone graft implant; and
    a third component comprising a polymeric coating extending over the implant;
    wherein the composite implant comprises a pore size distribution including at least a nanoporosity, and wherein the composite implant is pliable.

2. The implant of claim 1, wherein the coating comprises an organic acid.

3. The implant of claim 1, wherein the coating comprises a mineralogical calcium source.

4. The implant of claim 3, wherein the mineralogical calcium source is a calcium salt.

5. The implant of claim 1, wherein the bioactive glass shell is porous.

6. The implant of claim 1, wherein the bioactive glass fibers are porous.

7. The implant of claim 1, wherein the bioactive glass granules are porous.

8. The implant of claim 1, wherein the bioactive glass granules have varying sizes.

9. The implant of claim 1, wherein the bioactive glass fibers have varying sizes.

* * * * *